(12) United States Patent
Satish et al.

(10) Patent No.: US 11,333,545 B2
(45) Date of Patent: May 17, 2022

(54) SYSTEM AND METHOD FOR ESTIMATING AN AMOUNT OF A BLOOD COMPONENT IN A VOLUME OF FLUID

(71) Applicant: Gauss Surgical, Inc., Menlo Park, CA (US)

(72) Inventors: Siddarth Satish, Redwood City, CA (US); Kevin J. Miller, Mountain View, CA (US); Peter S. Hyoung, Los Altos, CA (US); Andrew T. Hosford, Idaho Falls, ID (US); Eric W. Hsieh, Los Altos, CA (US)

(73) Assignee: Gauss Surgical, Inc., Menlo Park, CA (US)

( * ) Notice: Subject to any disclaimer, the term of this patent is extended or adjusted under 35 U.S.C. 154(b) by 59 days.

(21) Appl. No.: 16/841,464

(22) Filed: Apr. 6, 2020

(65) Prior Publication Data

US 2020/0232841 A1 Jul. 23, 2020

Related U.S. Application Data

(63) Continuation of application No. 15/389,365, filed on Dec. 22, 2016, now Pat. No. 10,641,644.
(Continued)

(51) Int. Cl.
*G01G 17/04* (2006.01)
*G01G 21/28* (2006.01)
(Continued)

(52) U.S. Cl.
CPC .......... *G01G 17/04* (2013.01); *A61M 1/0001* (2013.01); *A61M 1/76* (2021.05); *G01G 21/28* (2013.01); *G01N 33/4925* (2013.01); *H04N 5/2253* (2013.01); *H04N 5/2257* (2013.01); *A61M 2205/3306* (2013.01);
(Continued)

(58) Field of Classification Search
CPC ........ G01G 17/04; G01G 21/28; G01G 19/52; A61M 1/76; A61M 1/0001; A61M 2205/3306; A61M 2205/3393; A61M 2205/3592; A61M 2205/3593; A61M 2205/50; A61M 2205/70; A61M 2230/20;
(Continued)

(56) References Cited

U.S. PATENT DOCUMENTS 2,707,955 A 5/1955 Borden
3,182,252 A 5/1965 Den
(Continued)

FOREIGN PATENT DOCUMENTS

CA 2870635 A1 10/2013
CN 101505813 A 8/2009
(Continued)

OTHER PUBLICATIONS

"U.S. Appl. No. 13/544,646, Notice of Allowance dated May 12, 2014", 10 pgs.
(Continued)

*Primary Examiner* — Randy W Gibson
(74) *Attorney, Agent, or Firm* — Howard & Howard Attorneys PLLC

(57) ABSTRACT

System and methods for analyzing the contents of a fluid canister are provided for use in healthcare settings. The system includes optical and weight sensors to analyze the canister contents.

41 Claims, 12 Drawing Sheets

Related U.S. Application Data

(60) Provisional application No. 62/387,234, filed on Dec. 23, 2015.

(51) Int. Cl.
*A61M 1/00* (2006.01)
*G01N 33/49* (2006.01)
*G01G 19/52* (2006.01)
*H04N 5/225* (2006.01)

(52) U.S. Cl.
CPC .............. *A61M 2205/3393* (2013.01); *A61M 2205/3592* (2013.01); *A61M 2205/50* (2013.01); *A61M 2205/70* (2013.01); *A61M 2230/20* (2013.01); *G01G 19/52* (2013.01)

(58) Field of Classification Search
CPC . H04N 5/2253; H04N 5/2257; G01N 33/4925
See application file for complete search history.

(56) References Cited

U.S. PATENT DOCUMENTS

| | | |
|---|---|---|
| 3,199,507 A | 8/1965 | Kamm |
| 3,367,431 A | 2/1968 | Prindle |
| 3,646,938 A | 3/1972 | Haswell |
| 3,687,209 A | 8/1972 | Goldberg et al. |
| 3,832,135 A | 8/1974 | Drozdowski et al. |
| 3,863,724 A | 2/1975 | Dalia, Jr. |
| 3,864,571 A | 2/1975 | Stillman et al. |
| 3,948,390 A | 4/1976 | Ferreri |
| 4,105,019 A | 8/1978 | Haswell |
| 4,149,537 A | 4/1979 | Haswell |
| 4,244,369 A | 1/1981 | Mcavinn et al. |
| 4,402,373 A | 9/1983 | Comeau |
| 4,422,548 A | 12/1983 | Cheesman et al. |
| 4,429,789 A | 2/1984 | Puckett, Jr. |
| 4,512,431 A | 4/1985 | Bloomfield |
| 4,562,842 A | 1/1986 | Morfeld et al. |
| 4,583,546 A | 4/1986 | Garde |
| 4,642,089 A | 2/1987 | Zupkas et al. |
| 4,681,571 A | 7/1987 | Nehring |
| 4,773,423 A | 9/1988 | Hakky |
| 4,784,267 A | 11/1988 | Gessler et al. |
| 4,832,198 A | 5/1989 | Alikhan |
| 4,917,694 A | 4/1990 | Jessup |
| 4,922,922 A | 5/1990 | Pollock et al. |
| 4,961,533 A | 10/1990 | Teller et al. |
| 5,014,798 A | 5/1991 | Glynn |
| 5,029,584 A | 7/1991 | Smith |
| 5,031,642 A | 7/1991 | Nosek |
| 5,048,683 A | 9/1991 | Westlake |
| 5,119,814 A | 6/1992 | Minnich |
| 5,119,830 A | 6/1992 | Davis |
| 5,128,036 A | 7/1992 | Svensson |
| 5,132,087 A | 7/1992 | Kristen et al. |
| 5,190,059 A | 3/1993 | Fabian et al. |
| 5,231,032 A | 7/1993 | Ludvigsen |
| 5,236,664 A | 8/1993 | Ludvigsen |
| 5,285,682 A | 2/1994 | Micklish |
| 5,348,533 A | 9/1994 | Papillon et al. |
| 5,369,713 A | 11/1994 | Schwartz et al. |
| 5,458,566 A | 10/1995 | Herrig et al. |
| 5,492,537 A | 2/1996 | Vancaillie |
| 5,522,805 A | 6/1996 | Vancaillie et al. |
| 5,568,262 A | 10/1996 | Lachapelle et al. |
| 5,595,456 A | 1/1997 | Berg et al. |
| 5,629,498 A | 5/1997 | Pollock et al. |
| 5,633,166 A | 5/1997 | Westgard et al. |
| 5,646,788 A | 7/1997 | Bietry |
| 5,650,596 A | 7/1997 | Morris et al. |
| 5,709,670 A | 1/1998 | Vancaillie et al. |
| 5,774,865 A | 6/1998 | Glynn |
| 5,807,358 A | 9/1998 | Herweck et al. |
| 5,851,835 A | 12/1998 | Groner |
| 5,923,001 A | 7/1999 | Morris et al. |
| 5,931,824 A | 8/1999 | Stewart et al. |
| 5,944,668 A | 8/1999 | Vancaillie et al. |
| 5,956,130 A | 9/1999 | Vancaillie et al. |
| 5,971,948 A | 10/1999 | Pages et al. |
| 5,984,893 A | 11/1999 | Ward |
| 5,996,889 A | 12/1999 | Fuchs et al. |
| 6,006,119 A | 12/1999 | Soller et al. |
| 6,061,583 A | 5/2000 | Ishihara et al. |
| 6,294,999 B1 | 9/2001 | Yarin et al. |
| 6,359,683 B1 | 3/2002 | Berndt |
| 6,510,330 B1 | 1/2003 | Enejder |
| 6,641,039 B2 | 11/2003 | Southard |
| 6,699,231 B1 | 3/2004 | Sterman et al. |
| 6,704,500 B2 | 3/2004 | Takematsu |
| 6,728,561 B2 | 4/2004 | Smith et al. |
| 6,730,054 B2 | 5/2004 | Pierce et al. |
| 6,777,623 B2 | 8/2004 | Ballard |
| 6,998,541 B2 | 2/2006 | Morris et al. |
| 7,001,366 B2 | 2/2006 | Ballard |
| 7,112,273 B2 | 9/2006 | Weigel et al. |
| 7,147,626 B2 | 12/2006 | Goodman et al. |
| 7,158,030 B2 | 1/2007 | Chung |
| 7,180,014 B2 | 2/2007 | Farber et al. |
| 7,274,947 B2 | 9/2007 | Koo et al. |
| 7,297,834 B1 | 11/2007 | Shapiro |
| 7,299,981 B2 | 11/2007 | Hickle |
| 7,364,545 B2 | 4/2008 | Klein |
| 7,384,399 B2 | 6/2008 | Ghajar |
| 7,430,047 B2 | 9/2008 | Budd et al. |
| 7,430,478 B2 | 9/2008 | Fletcher-Haynes et al. |
| 7,469,727 B2 | 12/2008 | Marshall |
| 7,499,581 B2 | 3/2009 | Tribble et al. |
| 7,557,710 B2 | 7/2009 | Sanchez et al. |
| 7,641,612 B1 | 1/2010 | Mccall |
| D611,731 S | 3/2010 | Levine |
| 7,670,289 B1 | 3/2010 | Mccall |
| 7,703,674 B2 | 4/2010 | Stewart et al. |
| 7,708,700 B2 | 5/2010 | Ghajar |
| 7,711,403 B2 | 5/2010 | Jay et al. |
| 7,749,217 B2 | 7/2010 | Podhajsky |
| 7,795,491 B2 | 9/2010 | Stewart et al. |
| 7,819,818 B2 | 10/2010 | Ghajar |
| 7,909,806 B2 | 3/2011 | Goodman et al. |
| 7,966,269 B2 | 6/2011 | Bauer et al. |
| 7,995,816 B2 | 8/2011 | Roger et al. |
| 8,025,173 B2 | 9/2011 | Michaels |
| 8,105,296 B2 | 1/2012 | Morris et al. |
| 8,181,860 B2 | 5/2012 | Fleck et al. |
| 8,194,235 B2 | 6/2012 | Kosaka et al. |
| 8,241,238 B2 | 8/2012 | Hiruma et al. |
| 8,279,068 B2 | 10/2012 | Morris et al. |
| 8,398,546 B2 | 3/2013 | Pacione et al. |
| 8,472,693 B2 | 6/2013 | Davis et al. |
| 8,479,989 B2 | 7/2013 | Fleck et al. |
| 8,576,076 B2 | 11/2013 | Morris et al. |
| 8,626,268 B2 | 1/2014 | Adler et al. |
| 8,693,753 B2 | 4/2014 | Nakamura |
| 8,704,178 B1 | 4/2014 | Pollock et al. |
| 8,792,693 B2 | 7/2014 | Satish et al. |
| 8,797,439 B1 | 8/2014 | Coley et al. |
| 8,897,523 B2 | 11/2014 | Satish et al. |
| 8,983,167 B2 | 3/2015 | Satish et al. |
| 9,047,663 B2 | 6/2015 | Satish et al. |
| 9,171,368 B2 | 10/2015 | Satish et al. |
| 9,595,104 B2 | 3/2017 | Satish et al. |
| 9,646,375 B2 | 5/2017 | Satish et al. |
| 9,652,655 B2 | 5/2017 | Satish et al. |
| 9,773,320 B2 | 9/2017 | Satish et al. |
| 9,936,906 B2 | 4/2018 | Satish et al. |
| 9,981,790 B1 | 5/2018 | Ost et al. |
| 10,641,644 B2 | 5/2020 | Satish et al. |
| 10,679,342 B2 * | 6/2020 | Nowicki ................ G01G 17/00 |
| 10,853,938 B2 * | 12/2020 | Sandmann ........... H04N 5/2252 |
| 2002/0124017 A1 | 9/2002 | Mault |
| 2003/0069509 A1 | 4/2003 | Matzinger et al. |
| 2003/0095197 A1 | 5/2003 | Wheeler et al. |
| 2003/0130596 A1 | 7/2003 | Goltz |
| 2004/0031626 A1 | 2/2004 | Morris et al. |

(56) References Cited

U.S. PATENT DOCUMENTS

| | | |
|---|---|---|
| 2004/0129678 A1 | 7/2004 | Crowley et al. |
| 2005/0051466 A1 | 3/2005 | Carter et al. |
| 2005/0163354 A1 | 7/2005 | Ziegler |
| 2005/0209585 A1 | 9/2005 | Nord et al. |
| 2005/0265996 A1 | 12/2005 | Lentz |
| 2006/0058593 A1 | 3/2006 | Drinan et al. |
| 2006/0178578 A1 | 8/2006 | Tribble et al. |
| 2006/0224086 A1 | 10/2006 | Harty |
| 2006/0241453 A1 | 10/2006 | Nguyen-Dinh et al. |
| 2007/0004959 A1 | 1/2007 | Carrier et al. |
| 2007/0008622 A1 | 1/2007 | Sommer |
| 2007/0108129 A1 | 5/2007 | Mori et al. |
| 2007/0243137 A1 | 10/2007 | Hainfeld |
| 2007/0287182 A1 | 12/2007 | Morris et al. |
| 2008/0029416 A1 | 2/2008 | Paxton |
| 2008/0030303 A1 | 2/2008 | Kobren et al. |
| 2008/0045845 A1 | 2/2008 | Pfeiffer et al. |
| 2008/0194906 A1 | 8/2008 | Mahony et al. |
| 2009/0076470 A1 | 3/2009 | Ryan |
| 2009/0257632 A1 | 10/2009 | Lalpuria et al. |
| 2009/0310123 A1 | 12/2009 | Thomson |
| 2009/0317002 A1 | 12/2009 | Dein |
| 2010/0003714 A1 | 1/2010 | Bachur, Jr. et al. |
| 2010/0007727 A1 | 1/2010 | Torre-Bueno |
| 2010/0025336 A1 | 2/2010 | Carter et al. |
| 2010/0027868 A1 | 2/2010 | Kosaka et al. |
| 2010/0066996 A1 | 3/2010 | Kosaka et al. |
| 2010/0087770 A1 | 4/2010 | Bock et al. |
| 2010/0150759 A1 | 6/2010 | Mazur et al. |
| 2010/0280117 A1 | 11/2010 | Patrick et al. |
| 2011/0066182 A1 | 3/2011 | Falus |
| 2011/0118647 A1 | 5/2011 | Paolini et al. |
| 2011/0144595 A1 | 6/2011 | Cheng |
| 2011/0192745 A1 | 8/2011 | Min |
| 2011/0196321 A1 | 8/2011 | Wudyka |
| 2011/0200239 A1 | 8/2011 | Levine et al. |
| 2011/0275957 A1 | 11/2011 | Bhandari |
| 2011/0305376 A1 | 12/2011 | Neff |
| 2011/0316973 A1 | 12/2011 | Miller et al. |
| 2012/0000297 A1 | 1/2012 | Hashizume et al. |
| 2012/0064132 A1 | 3/2012 | Aizawa et al. |
| 2012/0065482 A1 | 3/2012 | Robinson et al. |
| 2012/0127290 A1 | 5/2012 | Tojo et al. |
| 2012/0210778 A1 | 8/2012 | Palmer et al. |
| 2012/0257188 A1 | 10/2012 | Yan et al. |
| 2012/0262704 A1 | 10/2012 | Zahniser et al. |
| 2012/0271170 A1 | 10/2012 | Emelianov et al. |
| 2012/0309636 A1 | 12/2012 | Gibbons et al. |
| 2012/0327365 A1 | 12/2012 | Makihira |
| 2013/0010094 A1 | 1/2013 | Satish et al. |
| 2013/0094996 A1 | 4/2013 | Janssenswillen |
| 2013/0170729 A1 | 7/2013 | Wardlaw et al. |
| 2013/0245599 A1 | 9/2013 | Williams et al. |
| 2013/0301901 A1 | 11/2013 | Satish et al. |
| 2013/0303870 A1 | 11/2013 | Satish et al. |
| 2013/0308852 A1 | 11/2013 | Hamsici et al. |
| 2014/0063180 A1 | 3/2014 | Sharma |
| 2014/0079297 A1 | 3/2014 | Tadayon et al. |
| 2014/0128838 A1 | 5/2014 | Satish et al. |
| 2014/0207091 A1 | 7/2014 | Heagle et al. |
| 2014/0330094 A1 | 11/2014 | Pacione et al. |
| 2015/0294460 A1 | 10/2015 | Satish et al. |
| 2015/0294461 A1 | 10/2015 | Satish et al. |
| 2015/0310634 A1 | 10/2015 | Babcock et al. |
| 2015/0354780 A1 | 12/2015 | Wang |
| 2016/0015602 A1 | 1/2016 | Panzini et al. |
| 2016/0027173 A1 | 1/2016 | Satish et al. |
| 2016/0123998 A1 | 5/2016 | Macintyre et al. |
| 2016/0228639 A1 | 8/2016 | Zin |
| 2016/0243314 A1 | 8/2016 | Rodiera Olive |
| 2016/0327427 A1 | 11/2016 | Briones et al. |
| 2016/0331282 A1 | 11/2016 | Satish et al. |
| 2017/0011276 A1 | 1/2017 | Mehring et al. |
| 2017/0023446 A1 | 1/2017 | Rietveld et al. |
| 2017/0184442 A1 | 6/2017 | Satish et al. |
| 2017/0189621 A1 | 7/2017 | Rodiera et al. |
| 2017/0351894 A1 | 12/2017 | Satish et al. |
| 2017/0352152 A1 | 12/2017 | Satish et al. |
| 2018/0104681 A1 | 4/2018 | Lee et al. |
| 2018/0154088 A1 | 6/2018 | Broselow |
| 2019/0008427 A1 | 1/2019 | Satish et al. |

FOREIGN PATENT DOCUMENTS

| | | |
|---|---|---|
| DE | 102009007733 A1 | 8/2010 |
| EP | 3393539 A1 | 10/2018 |
| JP | S59161801 U | 10/1984 |
| JP | 61176357 A | 8/1986 |
| JP | 62144652 A | 6/1987 |
| JP | H03223629 A | 10/1991 |
| JP | H06510210 A | 11/1994 |
| JP | H07308312 A | 11/1995 |
| JP | 1137845 A | 2/1999 |
| JP | 2000227390 A | 8/2000 |
| JP | 2001050792 A | 2/2001 |
| JP | 2002331031 A | 11/2002 |
| JP | 2003075436 A | 3/2003 |
| JP | 2005052288 A | 3/2005 |
| JP | 3701031 B2 | 9/2005 |
| JP | 2006280445 A | 10/2006 |
| JP | 2008055142 A | 3/2008 |
| JP | 2008519604 A | 6/2008 |
| JP | 2009535639 A | 10/2009 |
| JP | 2010516429 A | 5/2010 |
| JP | 2011036371 A | 2/2011 |
| JP | 2011515681 A | 5/2011 |
| JP | 2011252804 A | 12/2011 |
| JP | 2014531570 A | 11/2014 |
| JP | 2019507615 A | 3/2019 |
| WO | WO-9217787 A1 | 10/1992 |
| WO | WO-9639927 A1 | 12/1996 |
| WO | WO-9710856 A1 | 3/1997 |
| WO | WO-2006053208 A1 | 5/2006 |
| WO | WO-2007129948 A1 | 11/2007 |
| WO | WO-2008094703 A2 | 8/2008 |
| WO | WO-2008094703 A3 | 8/2009 |
| WO | WO-2009117652 A1 | 9/2009 |
| WO | WO-2011019576 A1 | 2/2011 |
| WO | WO-2011145351 A1 | 11/2011 |
| WO | WO-2013009709 A2 | 1/2013 |
| WO | WO-2013172874 A1 | 11/2013 |
| WO | WO-2013173356 A1 | 11/2013 |
| WO | WO-2014013213 A1 | 1/2014 |
| WO | WO-2013009709 A3 | 5/2014 |
| WO | WO-2014099629 A1 | 6/2014 |
| WO | WO-2015161003 A1 | 10/2015 |
| WO | WO-2015160997 A1 | 10/2015 |
| WO | WO-2016187071 A1 | 11/2016 |
| WO | WO-2017111324 A1 | 6/2017 |
| WO | WO-2017112913 A1 | 6/2017 |

OTHER PUBLICATIONS

"U.S. Appl. No. 13/544,664, Final Office Action dated Feb. 12, 2016", 10 pgs.

"U.S. Appl. No. 13/544,664, Non Final Office Action dated Aug. 2, 2016", 7 pgs.

"U.S. Appl. No. 13/544,664, Non Final Office Action dated Aug. 13, 2015", 9 pgs.

"U.S. Appl. No. 13/544,664, Notice of Allowance dated Feb. 15, 2017", 10 pgs.

"U.S. Appl. No. 13/544,679, Non Final Office Action dated May 9, 2014", 9 pgs.

"U.S. Appl. No. 13/544,679, Notice of Allowance dated Sep. 3, 2014", 8 pgs.

"U.S. Appl. No. 13/738,919, Non Final Office Action dated Sep. 5, 2014", 8 pgs.

"U.S. Appl. No. 13/738,919, Notice of Allowance dated Nov. 10, 2014", 10 pgs.

"U.S. Appl. No. 13/894,054, Final Office Action dated Aug. 26, 2016", 7 pgs.

(56) References Cited

OTHER PUBLICATIONS

"U.S. Appl. No. 13/894,054, Non Final Office Action dated Mar. 30, 2016", 9 pgs.
"U.S. Appl. No. 13/894,054, Non Final Office Action dated Apr. 20, 2017", 7 pgs.
"U.S. Appl. No. 14/613,807, Non Final Office Action dated Mar. 20, 2015", 8 pgs.
"U.S. Appl. No. 14/613,807, Notice of Allowance dated Jun. 25, 2015", 10 pgs.
"U.S. Appl. No. 14/687,862, Non Final Office Action dated Mar. 24, 2017", 22 pgs.
"U.S. Appl. No. 14/687,862, Notice of Allowance dated Aug. 8, 2017", 6 pgs.
"U.S. Appl. No. 14/876,628, Final Office Action dated Jul. 26, 2016", 5 pgs.
"U.S. Appl. No. 14/876,628, Non Final Office Action dated Dec. 15, 2015", 8 pgs.
"U.S. Appl. No. 14/876,628, Notice of Allowance dated Oct. 26, 2016", 11 pgs.
"U.S. Appl. No. 15/154,917, Non Final Office Action dated May 9, 2019", 7 pgs.
"U.S. Appl. No. 15/389,365, Final Office Action dated Feb. 4, 2019", 23 pgs.
"U.S. Appl. No. 15/389,365, Non Final Office Action dated Jul. 13, 2018", 17 pgs.
"U.S. Appl. No. 15/389,365, Notice of Allowance dated Jan. 15, 2020", 8 pgs.
"U.S. Appl. No. 15/389,365, Notice of Allowance dated Aug. 28, 2019", 5 pgs.
"U.S. Appl. No. 15/389,365, Response filed Jan. 11, 2019 to Non Final Office Action dated Jul. 13, 2018", 21 pgs.
"U.S. Appl. No. 15/389,365, Response filed Aug. 1, 2019 to Final Office Action dated Feb. 4, 2019", 19 pgs.
"U.S. Appl. No. 15/389,365, Supplemental Notice of Allowability dated Jan. 27, 2020", 3 pgs.
"U.S. Appl. No. 15/416,986, Non Final Office Action dated Apr. 11, 2018", 7 pgs.
"U.S. Appl. No. 15/594,017, Non Final Office Action dated Feb. 21, 2019", 24 pgs.
"Blood loss measurement: Technology opportunity assessment", Merck for Mother's Program, (2012), 9 pgs.
"European Application Serial No. 12810640.8, Extended European Search Report dated Apr. 1, 2015", 8 pgs.
"European Application Serial No. 13790449.6, Extended European Search Report dated Nov. 17, 2015", 7 pgs.
"European Application Serial No. 13790688.9, Extended European Search Report dated Nov. 23, 2015", 9 pgs.
"European Application Serial No. 15780590.4, Extended European Search Report dated Sep. 18, 2017", 8 pgs.
"European Application Serial No. 16183350.4, Extended European Search Report dated Nov. 4, 2016", 8 pgs.
"European Application Serial No. 16880130.6, Extended European Search Report dated Sep. 4, 2019", 9 pgs.
"European Application Serial No. 16880130.6, Response filed Mar. 17, 20 to Extended European Search Report dated Sep. 4, 2019", 22 pgs.
"European Application Serial No. 16880130.6, Response to Communication pursuant to Rules 161(2) and 162 EPC filed Mar. 5, 2019", 9 pgs.
"European Application Serial No. 19156549.8, Extended European Search Report dated Jul. 12, 2019", 8 pgs.
"International Application Serial No. PCT/US2012/045969, International Search Report dated Sep. 17, 2012", 2 pgs.
"International Application Serial No. PCT/US2012/045969, Written Opinion dated Sep. 17, 2012", 4 pgs.
"International Application Serial No. PCT/US2013/021075, International Search Report dated Mar. 26, 2013", 2 pgs.
"International Application Serial No. PCT/US2013/021075, Written Opinion dated Mar. 26, 2013", 6 pgs.
"International Application Serial No. PCT/US2013/040976, International Search Report dated Sep. 24, 2013", 2 pgs.
"International Application Serial No. PCT/US2013/040976, Written Opinion dated Sep. 24, 2013", 4 pgs.
"International Application Serial No. PCT/US2015/026042, International Search Report dated Jul. 8, 2015", 2 pgs.
"International Application Serial No. PCT/US2015/026042, Written Opinion dated Jul. 8, 2015", 4 pgs.
"International Application Serial No. PCT/US2016/032561, International Search Report dated Aug. 18, 2016", 2 pgs.
"International Application Serial No. PCT/US2016/032561, Written Opinion dated Aug. 18, 2016", 5 pgs.
"International Application Serial No. PCT/US2016/068452, International Preliminary Report on Patentabilty dated Jul. 5, 2018", 11 pgs.
"International Application Serial No. PCT/US2016/068452, International Search Report dated Mar. 8, 2017", 3 pgs.
"International Application Serial No. PCT/US2016/068452, Written Opinion dated Mar. 8, 2017", 9 pgs.
"Optimizing protocols in obstetrics", ACOG, Series 2, (2012), 25 pgs.
"Quantification of blood loss: AWHONN practice brief No. 1", AWHONN Practice Brief, (2014), 1-3.
Adkins, A R, et al., "Accuracy of blood loss estimations among anesthesia providers", AANA Journal 82, (2014), 300-306.
Aklilu, A, "Gauss Surgical Measures Blood Loss with a Smartphone", [Online], Retrieved from the Internet: <http://www.health2con.com/news/2012/06/14/gauss-surgical-measures-blood-loss-with-a-smartphone>, (Jun. 14, 2012).
Al-Kadri, H M, et al., "Effect of education and clinical assessment on the accuracy of postpartum blood loss estimation", BMC Preq. Childbirth 14, 110, 7 pgs.
Bellad, et al., "Standardized Visual Estimation of Blood Loss during Vaginal Delivery with its Correlation Hematocrit Changes—A Descriptive Study", South Asian Federation of Obstetrics and Gynecology 1.1, (2009), 29-34.
Bose, P, et al., "Improving the accuracy of estimated blood loss at obstetric haemorrhage using clinical reconstructions", BJOG 113(8), (2006), 919-924.
Eipe, N, et al., "Perioperative blood loss assessment—How accurate?", Indian J. Anaesth. 50(1), (2006), 35-38.
Habak, P J, et al., "A comparison of visual estimate versus calculated estimate of blood loss at vaginal delivery", British J. Med. Medical Res. 11(4), (2016), 1-7.
Holmes, A A, et al., "Clinical evaluation of a novel system for monitoring surgical hemoglobin loss", Anesth. Analg. 119, (2014), 588-594.
Jones, R, "Quantitative measurement of blood loss during delivery", AWHONN, (2015), S41.
Kamiyoshihara, M, et al., "The Utility of an Autologous Blood Salvage System in Emergency Thoracotomy for a Hemothorax After Chest Trauma", Gen. Thorac. Cardiovasc. Surg. 56, (2008), 222.
Lyndon, A, et al., "Blood loss: Clinical techniques for ongoing quantitative measurement", CMQCC Obstetric Hemorrhage Toolkit, (2010), 1-7.
Lyndon, A, et al., "Cumulative quantitative assessment of blood loss", CMQCC Obstetric Hemorrhage Toolkit Version 2.0, (2015), 80-85.
Manikandan, D, et al., "Measurement of blood loss during adenotonsillectomy in children and factors affecting it", Case Reports in Clinical Medicine 4, (2015), 151-156.
Pogorelc, D, "iPads in the OR: New Mobile Platform to Monitor Blood Loss During Surgery", MedCityNews, [Online], Retrieved from the Internet: <http://medcitynews.com/2012/06/ipads-in-the-or-new-mobile-platform-to-monitor-blood-loss-during-surgery>, (Jun. 6, 2012), 4 pgs.
Roston, R B, et al., "Chapter 9: Blood loss: Accuracy of visual estimation", A comprehensive textbook of postpartum hemorrhage: An essential clinical reference for effective management 2nd edition, Sapiens, (2012), 71-72.

(56) References Cited

OTHER PUBLICATIONS

Sant, et al., "Exsanguinated Blood vol. Estimation Using Fractal Analysis of Digital Images", Journal of Forensic Sciences 57, (2012), 610-617.
Satish, S, et al., "System and Methods for Managing Blood Loss of a Patient", U.S. Appl. No. 15/943,561, filed Apr. 2, 2018, 66 pgs.
Schorn, M N, et al., "Measurement of blood loss: Review of the literature", J. Midwifery and Women's Health 55, (2010), 20-27.
Sukprasert, M, et al., "Increase accuracy of visual estimation of blood loss from education programme", J. Med. Assoc. Thai 89, (2006), S54-S59.
"European Application Serial No. 16880130.6, Communication Pursuant to Article 94(3) EPC dated Mar. 23, 2021", 6 pgs.
"Japanese Application Serial No. 2018-532640, Notification of Reasons for Refusal dated May 18, 2021", w/ English Translation, 6 pgs.
"Japanese Application Serial No. 2018-532640, Response filed Feb. 17, 2021 to Notification of Reasons for Refusal dated Nov. 24, 2020", w/ English claims, 15 pgs.
"Japanese Application Serial No. 2018-532640, Notification of Reasons for Refusal dated Nov. 24, 2020", with English translation, 6 pgs.
"European Application Serial No. 16880130.6, Response filed Jul. 20, 2021 to Communication Pursuant to Article 94(3) EPC dated Mar. 23, 2021", 17 pgs.
"Japanese Application Serial No. 2018-532640, Response filed Aug. 6, 2021 to Notification of Reasons for Refusal dated May 18, 2021", with machine translation, 9 pgs.

\* cited by examiner

SYSTEM AND METHOD FOR ESTIMATING AN AMOUNT OF A BLOOD COMPONENT IN A VOLUME OF FLUID

CROSS-REFERENCE TO RELATED APPLICATIONS

This application is a continuation of prior U.S. application Ser. No. 15/389,365, filed on Dec. 22, 2016, and claims priority to U.S. Provisional Patent Application No. 62/387,234, filed on Dec. 23, 2015, both of which are hereby incorporated by reference in their entirety. These applications are also related to U.S. patent application Ser. No. 13/544,664, filed on Jul. 9, 2012, and issued as U.S. Pat. No. 9,652,655 on May 16, 2017, and to U.S. patent application Ser. No. 13/738,919, filed on Jan. 10, 2013, issued as U.S. Pat. No. 8,983,167 on Mar. 17, 2015, both of which are hereby incorporated by reference in their entirety.

TECHNICAL FIELD

This invention relates generally to the field of blood loss management and more specifically to a new and useful system and method for estimating an amount of a blood component in a volume of fluid in the field of blood loss management.

SUMMARY

In one example, a system for assessing a fluid canister is provided, comprising a mounting structure with a canister recess and an imaging device recess, an inter recess wall between the canister recess and the imaging device recess, a scale coupled to the mounting structure and configured with at least one measurement element in communication with the canister recess, and a scale communication module configured to transmit weight information from the scale to a computing device. The measurement element may comprise a piezoelectric element. The imaging device recess may comprise a data interface in wired communication with the communication module. The system may further comprise a first aperture located in the inter-recess inter-recess wall. The first aperture may include a window and seal between the window and the inter-recess wall. The system may further comprise a second aperture located in the inter-recess wall. The inter-recess wall may comprise a curved portion with a concave surface facing the canister recess. The inter-recess wall may further comprise a flat portion facing the imaging device recess. The canister recess may comprise a movable surface. The system may further comprise a fluid canister configured to removably reside in the canister recess, and wherein the reflective insert may be configured to reside inside the fluid canister. The system may further comprise a reflective insert configured to reside within the fluid canister. The inter-recess wall may comprise a first aperture located at a vertical height corresponding to the reflective insert when placed at a bottom of the fluid canister when the fluid canister may be fully seated in the canister recess. The fluid canister may have a frusto-conical shape. The inter-recess wall has a vertical angle matching a frusto-conical angle of the fluid canister. The system may further comprise an imaging device configured to be removably inserted into the imaging device recess. The imaging device may be a computing device comprising an imaging assembly configured to acquire canister images from canister located in the canister recess and a processor configured to receive weight information from the communication module. The processor may be further configured to acquire a canister image with the imaging assembly upon detecting a weight change using the weight information. The computing device may further comprise a computing communication module configured to transmit the canister images and weight information from the computing device. The fluid canister may comprise an inlet and an outlet, wherein the outlet may be configured to be coupled to a vacuum source. The computing device may be configured to acquire canister images at the same acquisition rate that the processor may be configured to acquire weight information. The acquisition rate may be in the range of about one acquisition every 1 to 5 seconds.

In another example, a method of assessing a fluid canister is provided, comprising detecting the weight a fluid canister attached to a vacuum system, generating an image of the fluid canister, and determining a hemoglobin value of the fluid canister using the image. The imaging may be initiated upon detecting a change in the weight of the fluid canister. The method may further comprise modifying the hemoglobin value using the weight. The method may further comprise draining the fluid canister, and setting a tare weight of the fluid canister after draining the fluid canister.

In still another example, a blood monitoring system is provided, comprising a canister, a mount, a weighing scale, an imaging system, and a processor, wherein the canister defines an internal volume and comprises a translucent section. The blood monitoring system may further comprise a reflective insert arranged within the internal volume and adjacent and offset from the translucent section. The mount may be configured to engage an exterior surface of the canister. The mount may define a first window configured to seal over the exterior surface of the canister proximal the translucent section. The mount may further define a second window adjacent the first window and configured to seal over the exterior surface of the canister proximal the translucent section. The first window may be substantially optically isolated from the second window. The weighing scale may be coupled to the mount and may be configured to output a signal corresponding to a weight of contents in the canister. The imaging system may comprise an optical emitter aligned with the first window and configured to illuminate the reflective insert through the translucent section of the canister. The imaging system may further comprise a camera aligned with the second window. The processor may be configured to transform an image captured by the camera into an estimated concentration of a blood component in a fluid within the canister and to estimate an amount of the blood component in the canister based on the estimated concentration of the blood component and an output of the weighing scale.

DESCRIPTION OF THE EMBODIMENTS

Figure 1:
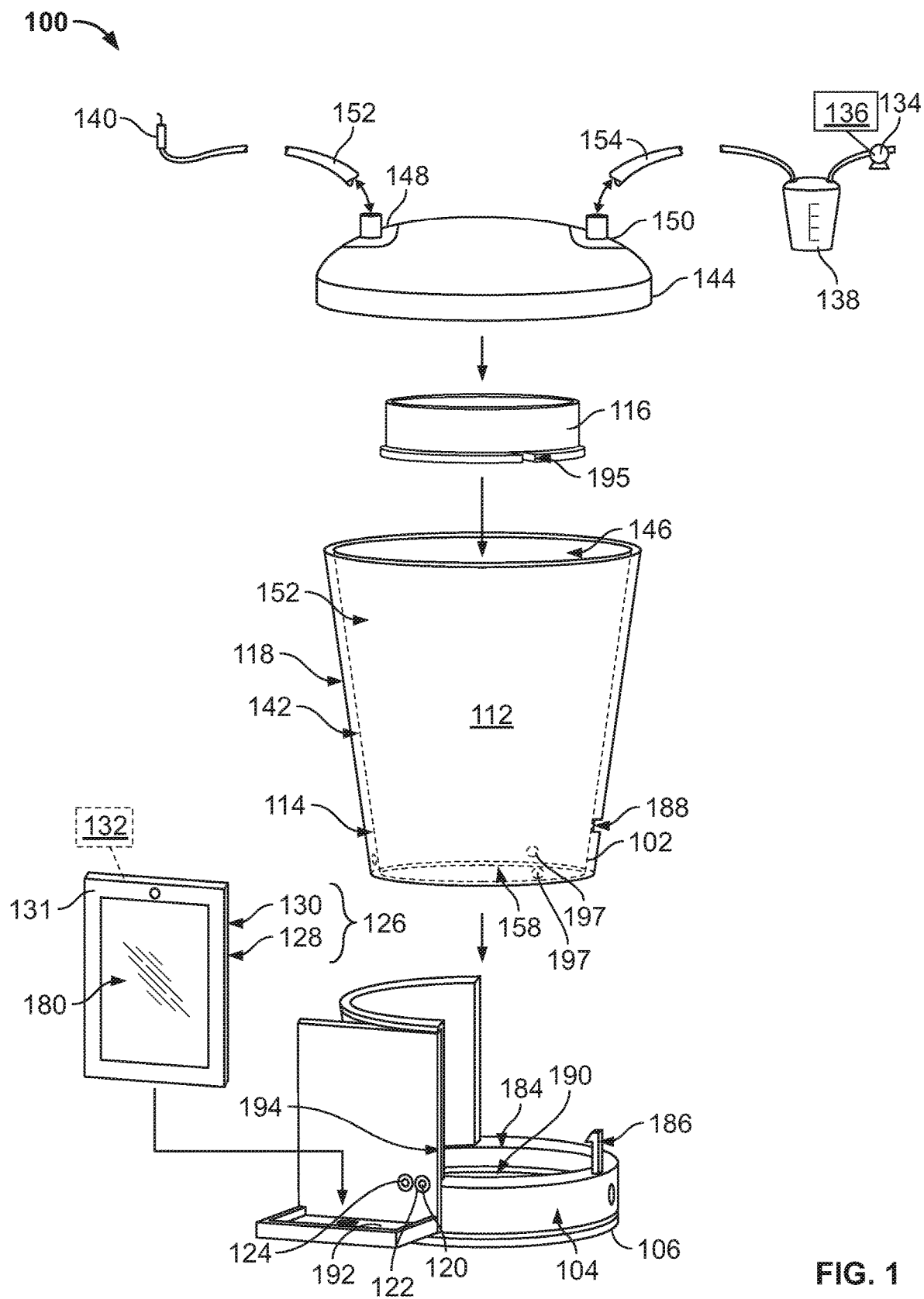
FIG. 1 is a schematic representation of a canister assessment system.

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. System

Generally, the system 100 includes a canister 102 configured to collect and hold fluid, an optical emitter 128 that illuminates fluid in the canister 102, a camera 130 that captures images of illuminated fluid, and a processor 132 that transforms color values contained in images captured by the camera 130 into estimations of a quality of fluid contained in the canister 102, such as a concentration of total hemoglobin, free hemoglobin, whole red blood cells, or whole blood, etc. in the fluid in the canister 102. The system also includes a weighing scale 106, and the system 100 can generate an estimation of a mass or volume of one or more blood components in the canister by merging an output of the weighing scale 106 with a blood component concentration thus estimated from color values in an image of the canister 102. For example, an estimate of the total hemoglobin content of the fluid in the canister may be calculated using the combination of the estimated concentration and volume of a blood component generated from the image and weight information from the scale, respectively.

In one particular example, as shown in FIG. 1, a system 100 for estimating an amount of a blood component in a volume of fluid includes a canister 102, a mount 104, a weighing scale 106, an imaging system 108, and a processor 132. The canister 102 defines an internal volume 112 and a translucent section 114 or wall, and may include a reflective insert 116 arranged within the internal volume 112 and adjacent and offset from the translucent section 114. The mount 104 is configured to engage an exterior surface 118 of the canister 102, and may comprise a first window 120 with a first seal 122a/b configured to seal over the exterior surface 118 of the canister 102 proximal the translucent section 114, and may further comprise a second window 124 adjacent the first window 120 and configured to seal over the exterior surface 118 of the canister 102 proximal the translucent section 114, wherein the first window 120 is substantially optically isolated from the second window 124, by the first seal 122a/b. The weighing scale 106 is coupled to the mount 104 and is configured to output a signal corresponding to a weight of contents in the canister 102. The imaging system 126 includes an optical emitter 128 aligned with the first window 120 and configured to illuminate the reflective insert 116 through the translucent section 114 of the canister 102, and also includes a camera 130 aligned with the second window. The imaging system components may be provided on a computing device 131. The processor 132 is in communication with the imaging system of the computing device 131 and is configured to transform an image captured by the camera 130 into an estimated concentration of a blood component in a fluid within the canister 102 and to estimate an amount or volume of the blood component in the canister 102 based on the estimated concentration of the blood component and an output of the weighing scale 106. In some examples, the processor 132 may be located in a remote computing system or cloud-based system, but in other examples, the processor 132 may be located or incorporated into the computing device 131.

In other variations, the scale 106 may also be used to detect other activity relating to the canister 102 and/or the fluid in the canister 102. For example, removal of the canister 102 may be detected so that the processor 132 can store the last or final concentration and volume information from the removed canister 102 and reset any counter(s) or register(s) for measuring any new canister.

1.1 Applications

The system 100 can be integrated into a surgical suction system within an operating room, surgical or procedure suite, emergency room, medical clinic, or other medical or health-related setting. In particular the system can interface with a primary canister and a suction wand in a surgical suction system to intermittently accumulate fluid collected with the suction wand, to capture an image of this fluid, to transform this image into an estimation of a quality of the fluid, and to then release its contents into the primary canister. For example, a vacuum pump 134 and regulator 136 coupled to a primary canister 138 can draw vacuum on the primary canister 138; the primary canister 138 can be fluidly coupled to the (intermediate) canister 102 of the system 100, and the suction wand 140 can be fluidly coupled to the (intermediate) canister 102 of the system 100 such that, when the vacuum pump 134 draws a vacuum on the primary canister 138, vacuum is communicated to the suction wand 140 via the (intermediate) canister 102 of the system 100. A nurse, anesthesiologist, surgeon, or other operator can thus manipulate the suction wand 140 to collect fluids from within and around a patient during a surgery and to dispense these fluids into the (intermediate) canister 102. The system 100 repeatedly captures and processes images of fluid in the canister 102 and samples the weighing scale 106 to generate updated fluid quality and quantity estimations throughout operations or procedures. In this example, once the (intermediate) canister 102 is full, its contents can be dispensed into the primary canister 138 for holding; the (intermediate) canister 102 can then be refilled via the suction wand 140 and its contents analyzed optically and/or by weight.

The system 100 can therefore be implemented in conjunction with a surgical wand and/or a primary (suction) canister within a surgical or other medical, clinical, or hospital setting to collect and image discrete volumes of blood and other bodily fluids. Components in the system that contact hazardous waste (e.g., blood, mucus, urine, etc.) can be disposable, and sensor and processing components of the system can be reusable. For example, the canister and the reflective insert can be used during a single operation or surgery and then disposed of, and the mount, weighing scale, imaging system, and processor can installed on multiple canisters across multiple surgeries over time to optically analyze qualities of fluids captured in these one-time-use canisters.

In other examples, the suction system may be attached to other vacuum systems, such as a negative pressure wound therapy system or a chest tube system, or an indwelling surgical draining tube, for assessing the amount and/or type of fluid loss or accumulation at those anatomical sites.

1.2 Canister

As noted previously, the intermediate canister 102 defines an internal volume 112 and a translucent section 114 or sidewall; and may include a reflective insert 116 configured to be inserted or arranged within the internal volume 112 and adjacent and offset from the translucent section 114. Generally, the canister 102 defines a vessel configured to collect fluid over time, includes a translucent or transparent material through which the imaging system 126 can illuminate contents of the vessel and capture images of contents of the vessel, and may include a reflective insert 116 (or reflective surface) that reflects and spreads light output from the imaging system 126 across a local volume of fluid to be imaged. The reflective insert 116 may cooperate with the wall 142 of the canister 102 to constrain a local volume of fluid in the canister 102 to a relatively shallow depth such that the imaging system 126 can capture color data through the full depth of this local volume of fluid (substantially) despite a concentration of red blood cells in the canister that may progressively block light transmission at greater depths. In some variations, the reflective insert 116 and the canister 102 may comprise recesses 195 and projections 197 configured to set the rotational orientation of the insert 116 and the canister 102.

In one implementation, the canister has a frusto-conical shape and is comprised of a substantially transparent polymer (e.g., polyethylene terephthalate, polymethyl methacrylate, polycarbonate, cellulose acetate butyrate) and may be configured to hold 3,000 milliliters of fluid. In other examples, the canister may have a capacity in the range of about 500 ml to 10,000 ml, or about 1,000 ml to 5,000 ml, or about 1,000 ml to 3,000 ml. The reflective insert may be comprised of any suitable material, for example, a polymer (e.g., white nylon, polycarbonate, polyethylene, polymethyl methacrylate) structure configured to sit in, or couple to, the bottom of the canister. In this implementation, the canister can include an engagement feature in its base or in the wall of the vessel proximal its base and configured to retain the reflective insert. In other variations, the canister may comprise a polygonal shape, a cylindrical shape, or other shape, including one with at least one planar side surface or wall.

Figure 4A:
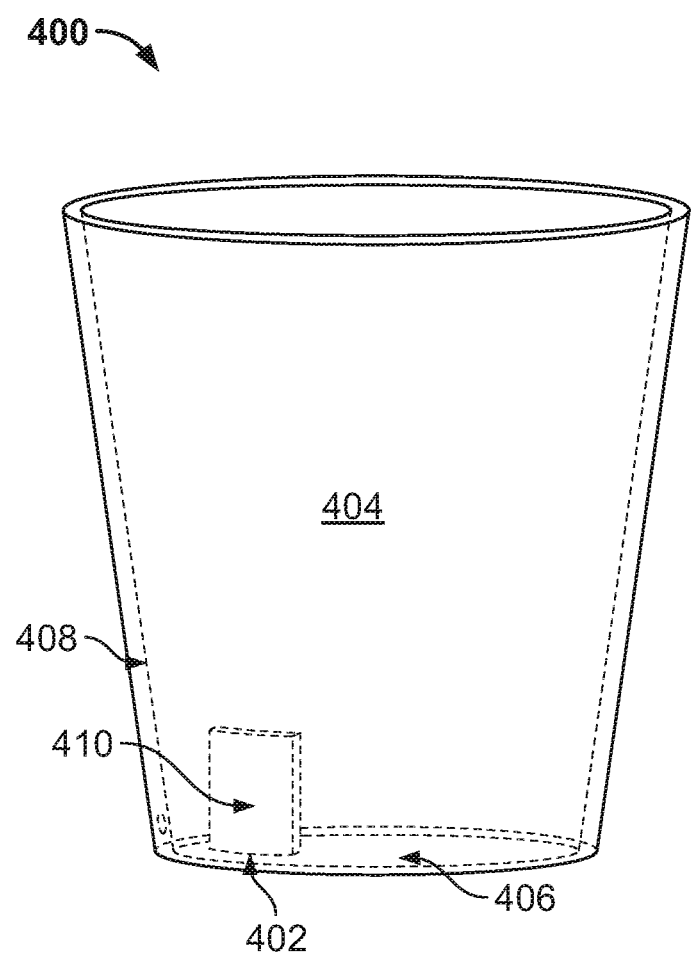
FIG. 4A to 4C are schematic examples of a fluid canister with an integrally formed reflective surface.
Figure 4B:
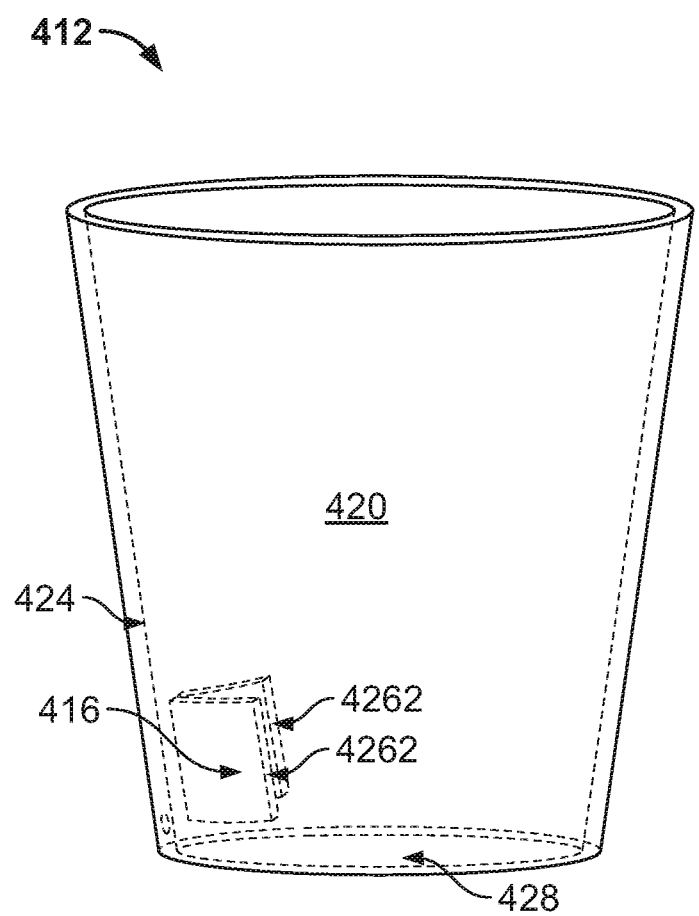
Figure 4C:
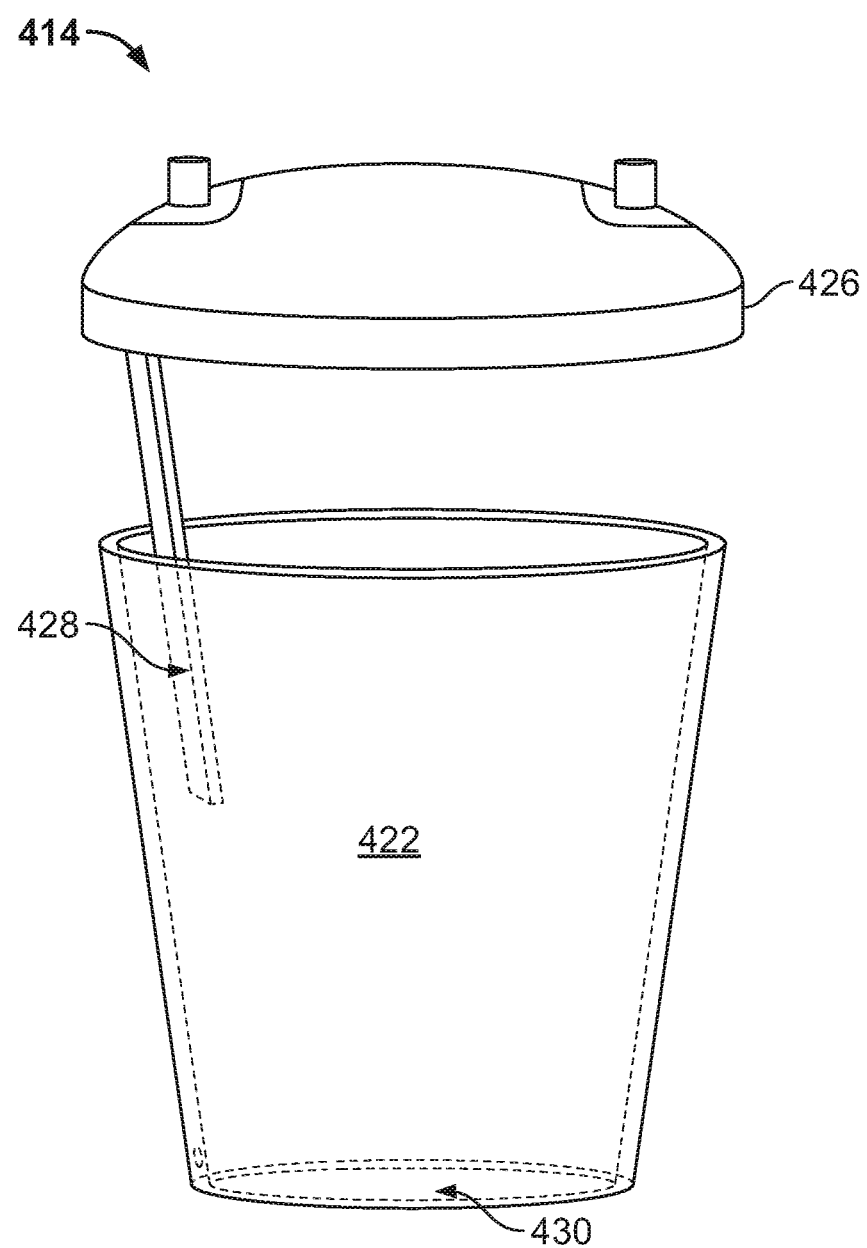

Alternatively, as depicted in FIG. 4A, the canister 400 may include a column 402 within the internal volume 404 of the canister 400 and extending upwardly from the base 406 of the frusto-conical vessel, offset inwardly from the interior wall 408 of the frusto-conical vessel, and backed or covered with a reflective material 410, or formed from a reflective material. In this implementation, the frusto-conical vessel and the column 402 can define a unitary structure (e.g., a drawn or molded polymer structure) with the base 406, and the column can thus function like the reflective insert to constrain a local volume of fluid in the canister to a shallow depth relative to the imaging system. However, the canister and the reflective insert (or corresponding surface integrated into the structure of the canister) can define any other geometry or include any other suitable material. The column may comprise a cylindrical shape, or may comprise a polygonal cross-sectional shape with at least one planar surface, such as a rectangle or square. In other embodiments, e.g., as depicted in FIGS. 4B and 4C, the canister 412, 414 may comprise a projection or outwardly facing interior wall 416, 418 within internal volume 420, 422 that is integrally formed with or attached to the sidewall 424 or lid 426 of the canister, 412, 414, respectively. For example, the canister 412 in FIG. 4B comprises a flanged arcuate wall 416 that is offset from the base 428 of the canister 412 and the sidewall 424 but attached at one or both edges 426 to the sidewall 424. The offset may permit the fluid level in the canister to rise between the sidewall 424 and the arcuate wall 416, while still permitting agitation of the base 428 of the canister 412. In FIG. 4C, the wall 428 is attached to the underside of the lid 426, and permits unimpeded fluid flow around the wall 428 as the internal volume 422 is filled, and also permits unimpeded agitation of the base 430 of the canister 414.

Figure 5A:
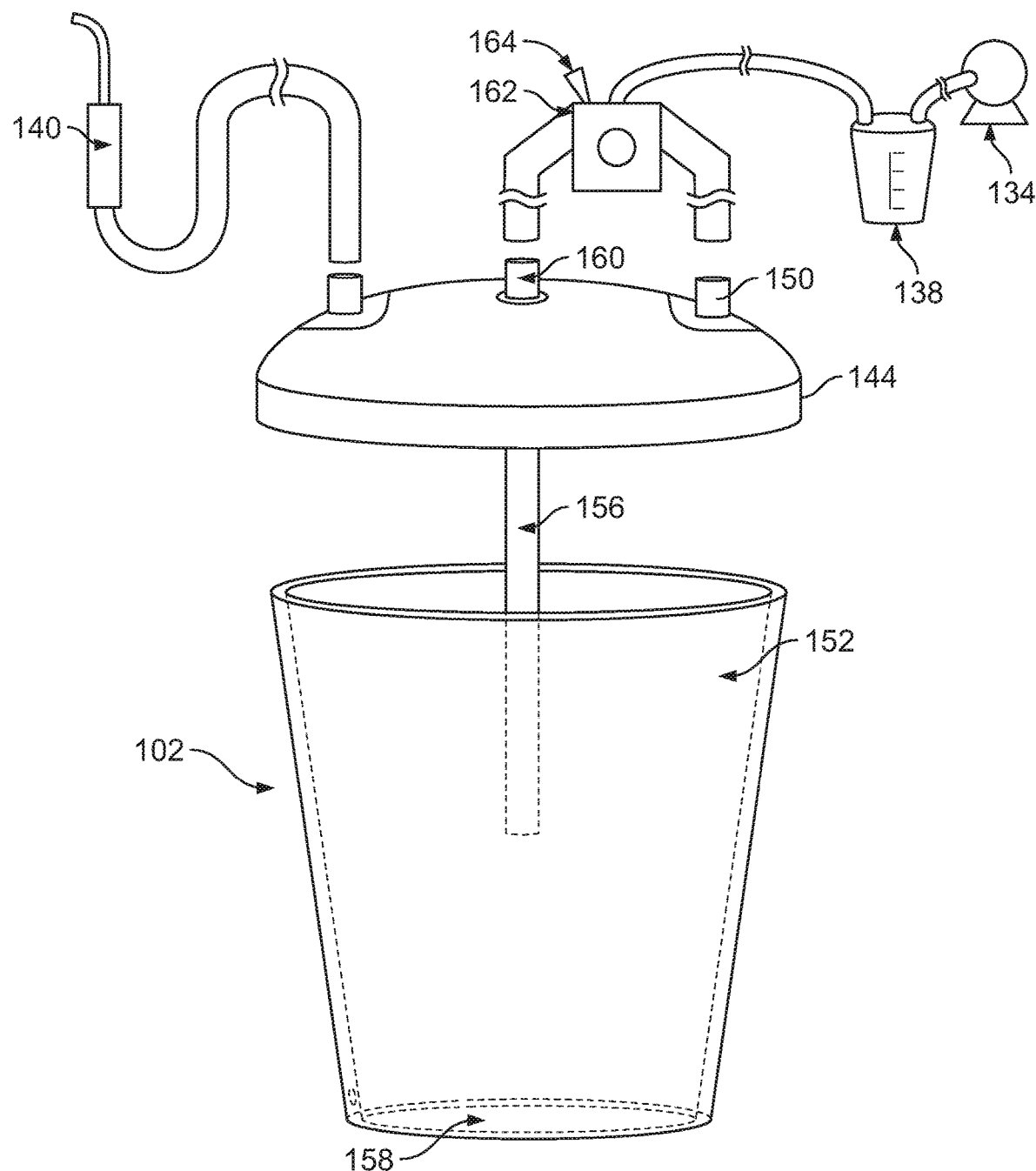
FIG. 5A is an example of a fluid canister with a sump pickup.

Referring back to FIG. 1, the system 100 can also include a lid 144 configured to cover and/or seal an upper opening 146 in the canister 102. In one implementation, the lid 144 includes an inlet port 148 configured to couple to a suction wand 140; and an outlet port 150 configured to couple to a vacuum pump 134 (via an optional primary canister 138) using vacuum lines 152, 154. In the implementation shown if FIG. 5A, the lid 144 is also depicted with an optional sump pickup 156 extending from the lid 144 to the base 158 of the canister 102 and in fluid communication with the vacuum port 160; and a two-way valve 162 configured to selectively connect the outlet port 150 to an upper volume 152 of the canister 102 in a first position and to the vacuum port 160 of the sump pickup 156 in a second position. In particular, with the valve 162 in the first position, the lid 144 can communicate vacuum from an external vacuum source 134 into the canister 102 just below lid 144. Thus, the canister can communicate vacuum to the suction wand 140 to draw fluid into the canister 102. However, when the valve 162 is in the second position, the lid 144 communicates vacuum from the external source 134 to the sump pickup 156 such that fluid is drawn up the sump pickup 156, through the vacuum port 160 in fluid communication with the sump pickup 156, and into a remote fluid collector (e.g., to a primary canister 138). In this implementation, the valve 162 can be manually actuated by a user on a switch 164 or button (or other mechanical mechanism on the valve 162) when the canister is sufficiently full of fluid in order to drain the contents of the canister into another container (e.g., a primary canister), or the system can automatically switch the valve between the first and second positions via a solenoid or other valve control mechanism, such as when the weighing scale 106 indicates that a threshold mass of fluid (corresponding to an approximate threshold volume of fluid in the canister based on an 160 estimated fluid density of ~1030 kg/m$^3$) is contained in the canister 102 or when an output state of a float sensor in the lid changes, thereby indicating that a preset fill level limit has been reached. Alternatively, the user may also control the valve electronically via the processor or other user interface. Also, although the valve 162 in FIG. 5A is depicted as separate from the lid 144, in other variations, the valve, the vacuum port to the sump pickup, and the fluid line therebetween may be integrally formed or housed within the lid, such that only an inlet to be attached to a suction wand or catheter, and an outlet port from the integrated valve, are provided on the lid. Where the valve is electronically controlled, a wired data interface may be provided on the lid, or a wireless communication module to the computer device may be provided.

Figure 5B:
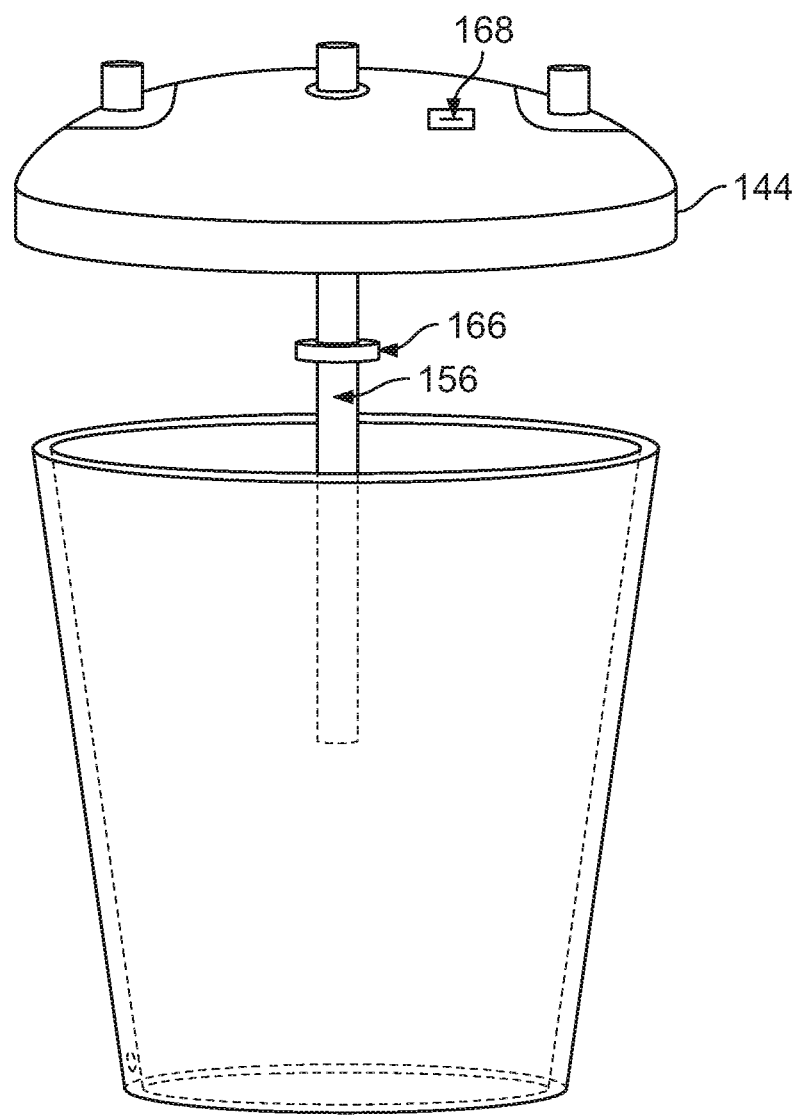
FIGS. 5B and 5C are examples of fluid canisters with a sump pickup and integrated float sensor and fluid level sensor, respectively.
Figure 5C:
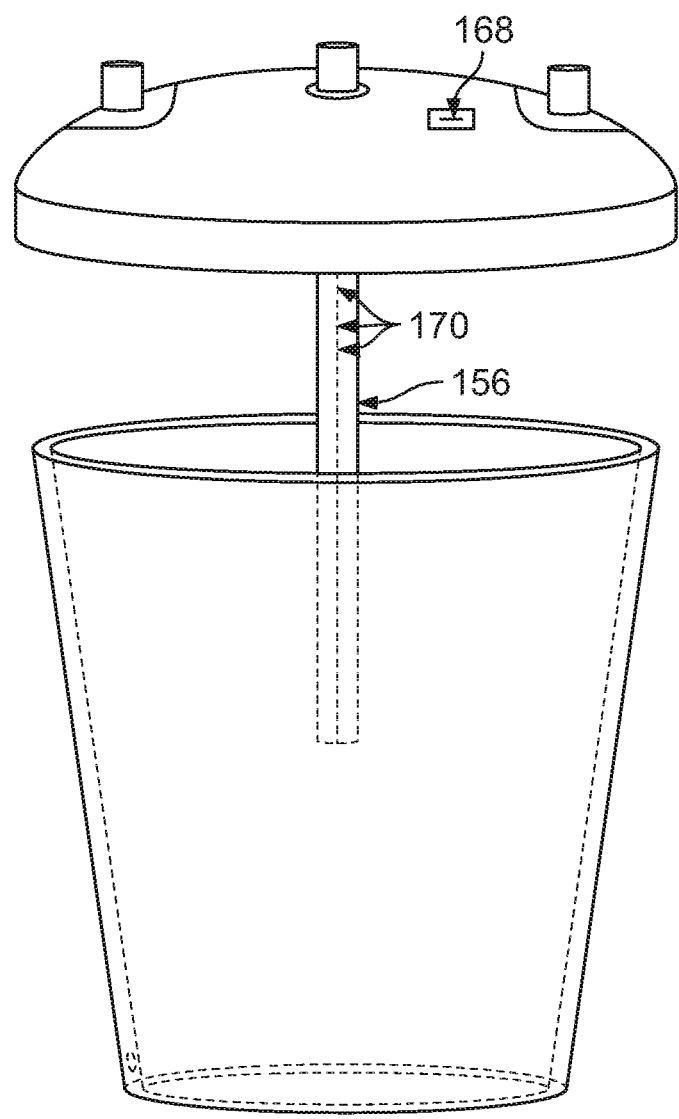

In the particular example in FIG. 5B, the fluid level sensor may comprise a float sensor mechanism 166 configured to travel up and down along the sump pickup 156. The float sensor mechanism 166 may be configured to close electrodes on the underside of the lid 144 upon reaching a designated fluid level, to provide a signal via a float signal interface 168 in communication with the processor to detect canister volume. In other variations, the float sensor mechanism may be a visual aid for the imaging system to detect the fluid level. In still other examples, the fluid level sensor may be comprise a series of fluid contact electrodes 170 as shown in FIG. 5C along the length of the sump pickup 156. Different pairings of the electrodes 168 may be checked via the float signal interface 168 in communication with the processor to determine the fluid level based upon the closed electrode loop formed by the fluid. The fluid level sensor may also be provided on a vertical structure separate from the sump pickup, including but not limited to the inner wall of the canister.

The scale 106 may also be used to detect other activity relating to the canister 102 For example, removal of the canister 102 may be detected so that the processor 132 can store the last or final concentration and volume information from the removed canister 102 and reset any counter(s) or register(s) for measuring any new canister. Weight oscillations resulting from intermittent suctioning of fluid when the suction wand 140 is adjacent to fluid-air interface may occur, and the processor may be configured omit or correct for transient peaks in the detected weight.

Figure 6A:
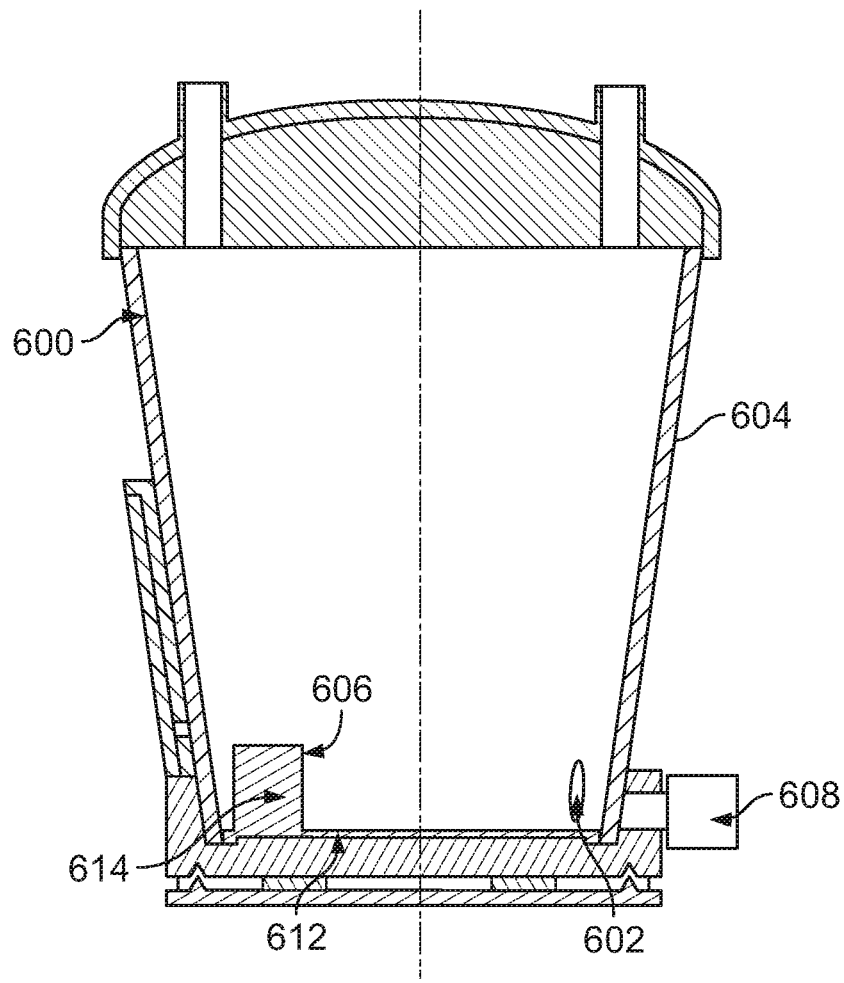
FIG. 6A is a side cross-sectional view of a fluid canister with a magnetic agitator.
Figure 6B:
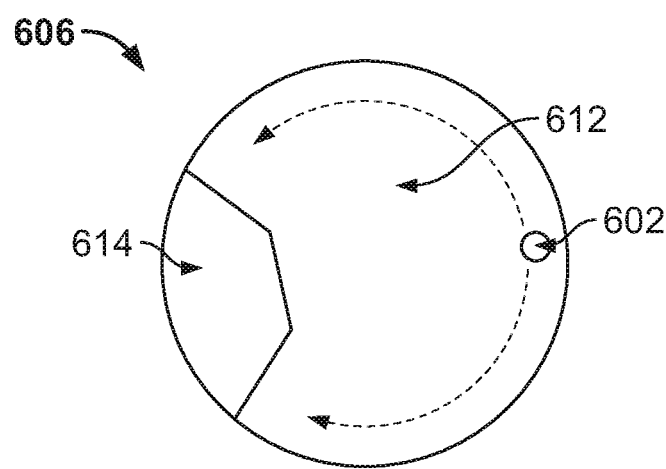
FIG. 6B is a superior schematic view of the reflective insert in FIG. 6A.

The canister can also include a disposable agitator element configured to be remotely actuated by an agitator driver in the mount. For example, the canister 600 depicted in FIG. 6A can include a magnetic stirring element 602 configured to run between the wall 604 of the canister 600 and the reflective insert 606 (or between the column extending from the base of the canister, as described above). In this example, when the agitator driver 608 in the mount 610 is actuated, the agitator driver 608 (e.g., a motor) can be magnetically coupled to the magnetic stirring element 602 through the wall 604 and can translate or draw the magnetic stirring element in an arc about the axis of the canister 600, between the wall of the canister and the reflective insert—to disrupt and redistribute sediment that may have collected in the bottom of the canister. FIG. 6B depicts a top view of the reflective insert 606 with a low-profile base 612 configured to sit on the base of the canister and a protruding reflective segment 614. In this variation the reflective surface does not form a complete 360 degree arc, so that the stirring element 602 may transmit some agitation force to the shallow region between the canister wall and the reflective segment 614. The agitator drive 608 may also be configured to spin the stirring element 602 as it translates the stirring element 602 back and forth along an arc path along the wall 604 of the canister 600. In this particular example, the agitator driver 608 is positioned about a sidewall of the mount 610, but in other examples, the agitator driver may be positioned about the lower wall of the mount. The agitator drive 608 may also be configured to spin the stirring element 602 as it translates the stirring element 602 back and forth along an arc path along the wall 604 of the canister 600. In this particular example, the agitator driver 608 is positioned about a sidewall of the mount 610, but in other examples, the agitator motor may be positioned about the lower wall of the mount or even on its base.

Figure 6C:
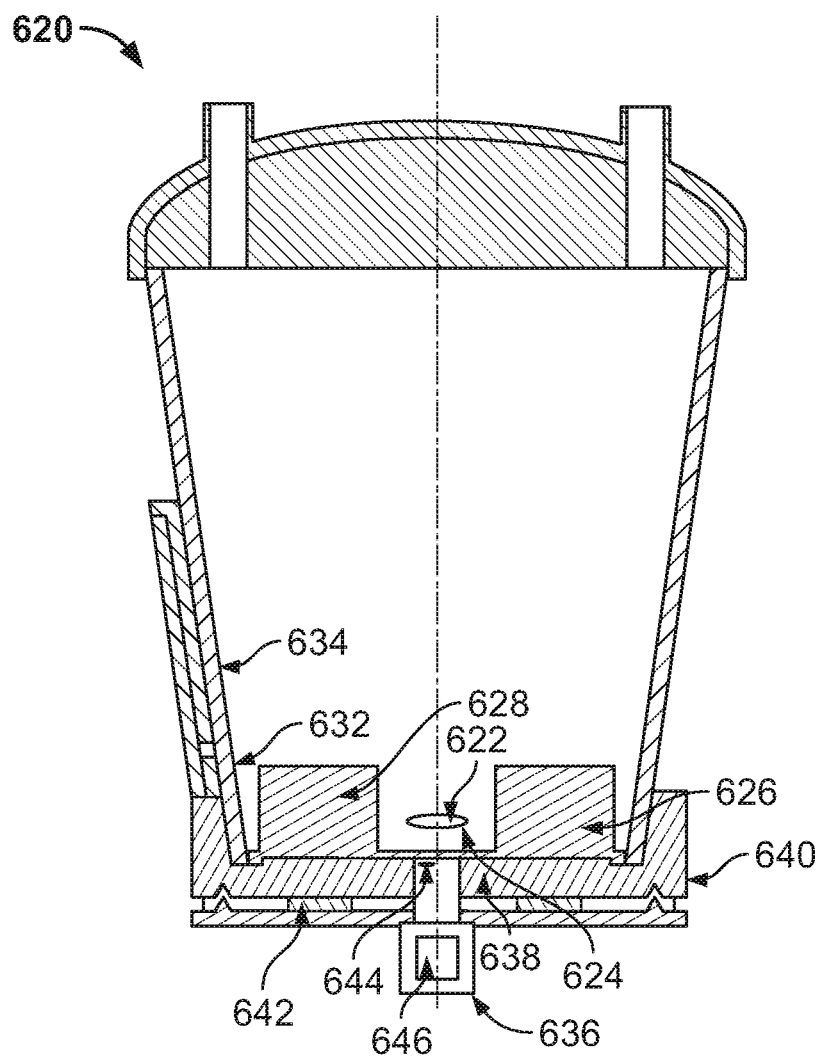
FIG. 6C is a side cross-sectional view of another fluid canister with a magnetic agitator.
Figure 6D:
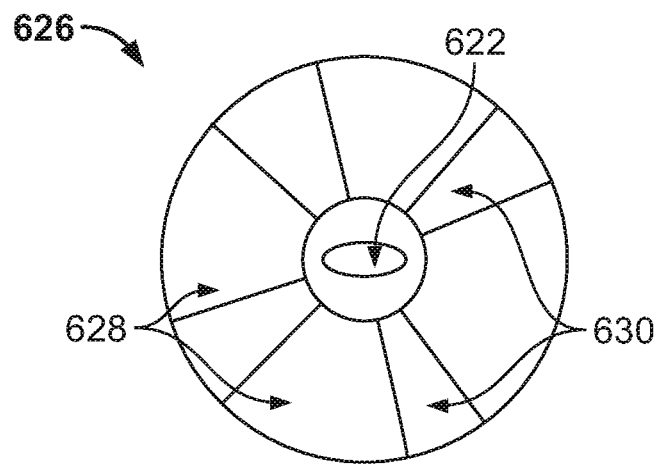
FIG. 6D is a is superior schematic view of the reflective insert in FIG. 6C.

In another example depicted in FIG. 6C, the canister 620 may include a centrally spinning magnetic stirring element 622 configured to reside in a central recess 624 of a ring-shaped reflective insert 626. As shown in FIG. 6D, the insert 626 may comprise segmented reflective structures 628 with radial flow spaces 530 therebetween to facilitate indirect mixing of the canister contents located in imaging region 632 of the canister 610 between the inner wall 634 and the segmented reflective structures 628. The agitator motor or driver 636 may be located in the bottom wall 638 of the mount 640, surrounded by the scale 642. In other configurations, however, the scale may be mounted below the agitator driver, and essentially monitors of the weight of the entire mount, computing device, canister and canister contents, such that prior to initiating blood monitoring, the tare weight of mount, computing device and empty canister is measured to provide a corrective value and zero the measured weight prior to fluid collection.

In another variation, depicted in FIGS. 6C and 6D, the mount 640 includes an agitator driver 636 configured to couple to an agitator element 622 arranged within the canister 620 For example, the agitator driver 636 can include a magnetic element 644 (e.g., an electromagnet, a rare-earth magnetic) eccentrically mounted to a rotary motor 646 arranged below the base 638 of the mount 640. In this example, the system can intermittently actuate the rotary motor 646, thereby rotating the magnetic element 644, which magnetically couples to and rotates the agitator element 622, thereby dispersing sediment collected on the base of the canister and/or agitating contents in the canister to achieve a more uniform mixture of fluid, solids, particulate, etc. (e.g., red blood cells, plasma, saline, fat, clotted blood, etc.) in the canister prior to imaging.

The centrally spinning magnetic stirring element 622 may be configured to reside in a central recess 624 of a ring-shaped reflective insert 626. As shown in FIG. 6D, the insert 626 may comprise segmented reflective structures 628 with radial flow spaces 530 therebetween to facilitate indirect mixing of the canister contents located in imaging region 632 of the canister 610 between the inner wall 634 and the segmented reflective structures 628. The agitator driver 636 may be located in the bottom wall 638 of the mount 640, surrounded by the scale 642. In other configurations, however, the scale may be mounted below the agitator driver, and essentially monitors of the weight of the entire mount, computing device, canister and canister contents, such that prior to initiating blood monitoring, the tare weight of mount, computing device and empty canister is measured to provide a corrective value and zero the measured weight prior to fluid collection.

Figure 6E:
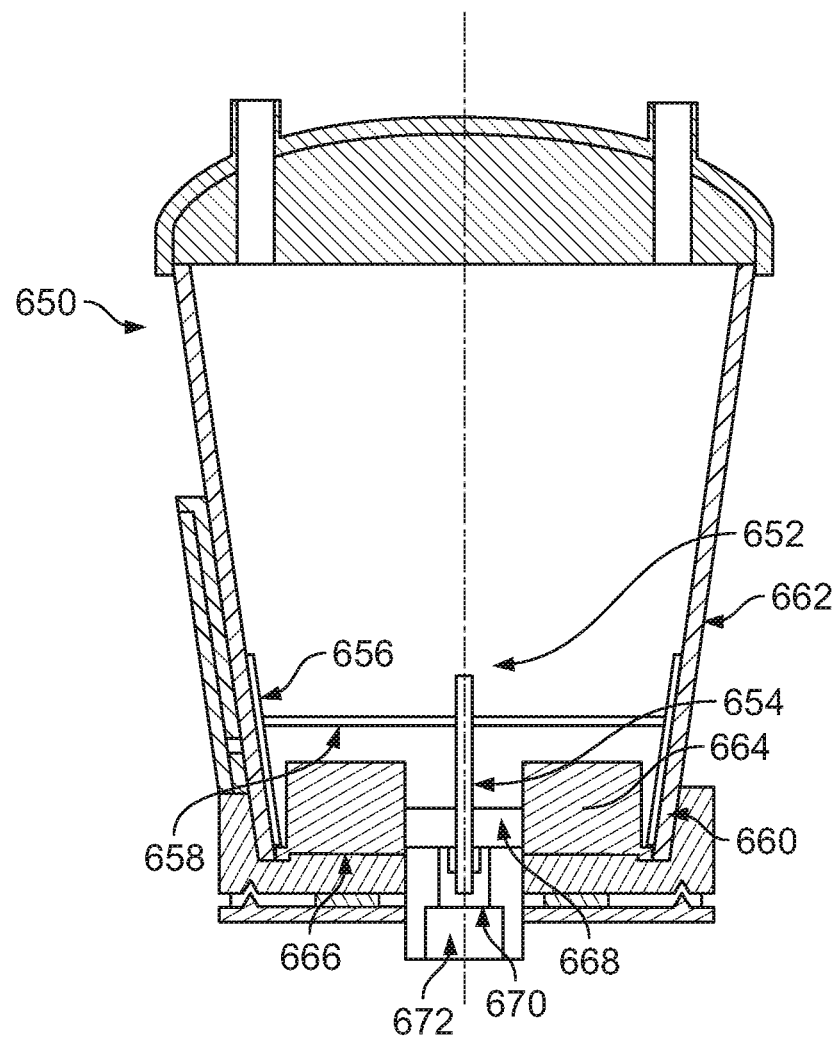
FIG. 6E is a side cross-sectional view of another fluid canister with a mechanical agitator.

In still another example depicted in FIG. 6E, the canister 650 comprises a rotatable paddle 652 with a central drive shaft 654 and vertical paddle elements 656 attached to the central drive shaft 644 via horizontal paddle elements 658. The vertical paddle elements 656 are configured to directly agitate the imaging space 660 between the wall 662 and the reflective structure 664. In this particular example, the drive shaft 644 protrudes from the base 666 of the canister 650 and a seal 688 is provided to resist canister leakage. The drive shaft 644 is received in a drive shaft recess 670 rotated by a motor 672.

However, the canister can include any other suitable type of agitator element remotely configured to be remotely actated to stir or redistribute contents of the canister. Additional examples are provided below.

1.3 Imaging System

Referring back to FIG. 1, the imaging system may generally include: an optical emitter 128 configured to illuminate the reflective insert 116 through the translucent section 114 of the canister 102; and a camera 130 configured to capture a digital photographic image of a volume of fluid contained in the canister 102. Generally, the camera 130 functions to capture digital color (e.g., photographic) images of a volume of fluid in the canister 102. For example, the camera 130 can include a digital (e.g., CMOS or CCD) RGB camera. The optical emitter 128 is typically offset (e.g., laterally) from the camera 130 and configured to illuminate a volume of fluid contained in the canister 102 for imaging by the camera 130. In particular, the optical emitter 128 may be configured to output a controlled amount of light (e.g., light flux, lumens) such that the camera 130 can repeatedly capture color data through a depth of the fluid in the canister 102 despite ambient lighting conditions. In particular, the optical emitter 128 may output sufficient light and camera 130 may capture images with sufficiently fast shutter speeds such that images captured by the camera contain color data of sufficiently quality to be transformed into sufficiently accurate estimations of the concentration of one or more blood components in the canister 102, and such that the effect of ambient light on the color of the volume of fluid recorded in an image is relatively insignificant.

In one implementation, the imaging system 126 may include a camera 130 and a flash element or optical emitter 128 integrated into a standalone computing device, such as a smartphone, a tablet, or a personal media player. In this implementation, the computing device can execute a native image processing application that locally performs the method described below. The computing device can also include a display 180, opposite the camera 130 and an optical emitter 128, and configured to display or render a weight or volume of contents of the canister 102, a composition of fluid contained in the canister 102 (e.g., a concentration or volume fraction of hemoglobin, red bloods cells, or whole blood, etc. in the canister); and/or notifications, such as a prompt to empty the canister if fluid in the canister is approaching a maximum fill level, a prompt to empty the canister or to stir the contents of the canister if sediment is obscuring the camera, or a prompt to salvage red blood cells from the contents of the canister, such as described below.

1.4 Mount

Figure 2A:
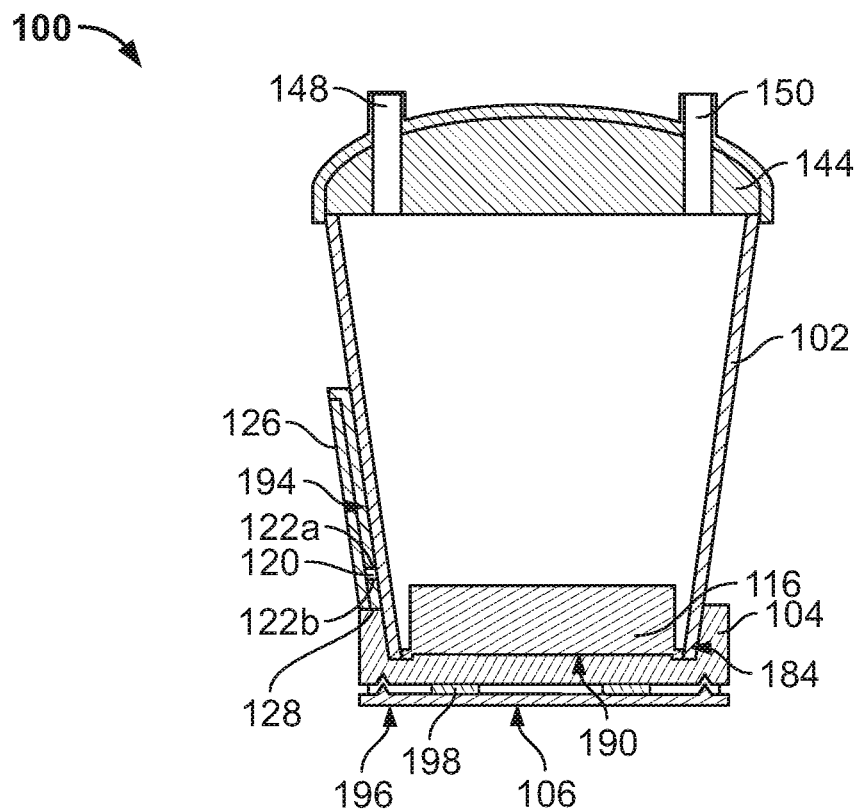
FIGS. 2A and 2B are schematic representations of one variation of a system described herein.
Figure 2B:
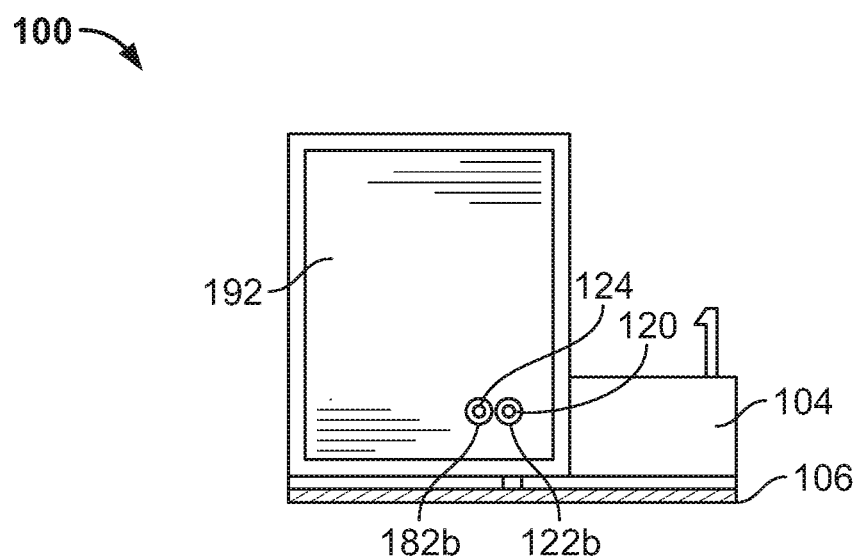

As shown in FIGS. 1, 2A and 2B, the mount 104 is typically configured to engage an exterior surface 118 of the canister 102. The mount 104 may also comprise or define a first window 120 configured with a first surrounding seal 122a/b to seal over the exterior surface 118 of the canister 102 proximal the translucent section 114, and to further comprise or define a second window 124 adjacent the first window 120 and configured with a second surrounding seal 182a/b to seal over the exterior surface 118 of the canister proximal the translucent section, wherein the first window is substantially optically isolated from the second window. Generally, the mount is configured to support the optical emitter 128 and the camera 130 adjacent and facing the canister 102 and to isolate the camera 130 from light outside of the canister, e.g., ambient light, light output by the optical emitter 128 but not reflected by or refracted through fluid in the canister 102.

The mount 104 is configured to receive and support the base 158 of the canister 102. In one example, the mount 104 defines a frusto-conical receptacle 184 sized to fit the canister 102, as shown in FIG. 2A, and includes an optional latch 186 configured to transiently mate with a recess or an engagement feature 188 on the vessel 102, thereby constraining the canister 102 in the mount. In this example, the canister 102 can be inserted into the receptacle 184, and the latch 186 can engage the canister 102 once the base 158 of the canister 102 meets the base 190 of the receptacle 184; the latch 186 can then be withdrawn to release the canister 102 for disposal or emptying. In a similar example, the mount can include a conical receptacle defining a conical angle matched to the conical angle of the canister. In this example, the canister can be inserted into the conical receptacle, and the weight of the canister can compress the walls of the canister against the interior surface of the conical receptacle. In another example, the mount includes a belted or elastic strap configured to wrap around a canister and to retain an interior surface of the mount against an exterior surface of the canister. The canister may also be configured with a groove or recess to receive the strap. In the foregoing examples, the mount can define first and second windows—for the optical emitter and the camera, respectively—that intersect the interior surface of the receptacle to meet the exterior surface of a canister when the canister is installed in the mount.

In one implementation, the mount 104 comprises a computing device receptacle 192 that is configured to transiently receive a standalone computing device 131 (as described above) and to support the computing device 131 with its camera 130 and optical emitter 128 or flash element facing the canister 102, as shown in FIG. 1. For example, the mount 104 can support the computing device 131 in a vertical orientation such that the optical axis of the camera 130 is substantially normal to an adjacent exterior surface 118 of the canister 102; proximal the base 158 of the canister 102 to optically detect and analyze a relatively small volume of fluid in the canister through the transparent region 114 of the canister 102 located between the canister wall 142 and the reflective insert 116, and vertically offset above the base 158 of the canister 102 such that a volume of sediment may collect on the base 158 of the canister 102 without immediately obscuring the optical emitter and/or the camera, as shown in FIG. 2A. The mount 104 can also support the computing device 131 at an offset from the wall 142 of the canister 102 such that a minimum width and/or height of the reflective insert 116 remains within the field of view of the camera 130.

However, the mount can define any other geometry or function in any other way to transiently couple the optical emitter and the camera to the canister, and vice versa. In some variations, the computing device receptacle may be a modular or adjustable receptacle, to permit the use of different computing devices with the system, e.g. an IOS, Android, Windows or Linux tablet/cellphone, or camera system. In some other variations, a lens may be provided in the optical path of the second window corresponding to the camera 130. A lens may facilitate focused image capture, which may be used to detect and/or characterize sediment or other materials found in the canister.

The mount 104 defines a first window 120 configured to align with the optical emitter 128 and a second window 124 configured to align with the camera 130. In particular, the first window 120 is configured to pass light from the optical emitter 128 to the wall 142 of the canister 102, which passes light into fluid in the canister 102 and onto the reflective insert 116, thereby illuminating the fluid and the reflective insert 116; the second window 124 is configured to pass light reflected and refracted out of the wall 142 of the canister 102 by the reflective insert 116 and the fluid into the camera 130. The mount 104 can include a first seal 122a around a perimeter of a first side of the first window 120 and configured to seal the first window 120 against the exterior surface 118 of the canister 102 when the canister 102 is installed in the mount 104; a second seal 122b around a perimeter of the opposite side of the first window 120 and configured to seal the first window 120 against an exterior surface of the computing device 131—around the optical emitter 128—when the computing device 131 is installed in the mount 104, as shown in FIG. 2B. In some examples, the first seal 122a and the second seal 122b may an integrally formed window seal or grommet spanning both surfaces of the window 120. Similarly, the mount can include: a third seal 182a around a perimeter of a first side of the second window 124 and configured to seal the second window 124 against the exterior surface 118 of the canister 102 when the canister 102 is installed in the mount 104; a fourth seal 182b around a perimeter of the opposite side of the second window 124 and configured to seal the second window 124 against an exterior surface 118 of the computing device 131—around the camera 130—when the computing device 131 is installed in the computing device receptacle 184 of the mount 104. The third and fourth seals 182a/b may be separate seals or an integrally formed window seal or grommet spanning both surfaces of the second windows 124. In some further examples, a single figure-eight seal may be used for the optical emitter 128 and camera 130. The seals 122a/b and 182a/b can include opaque flexible seals to minimize crosstalk (e.g., light bleed) between the optical emitter 128 and the camera 130 outside of the canister 102. For example, the mount 104 can include soft, black silicone O-rings configured to abut and compress between the inter-recess wall structure 194 of the mount 104 and the canister 102 (e.g., the first and third seals 122a, 182a) and to abut and compress between the inter-recess wall structure 194 of the mount 104 and the computing device 131 (e.g., the second and fourth seals 122b, 182b).

1.5 Weighing Scale

Referring back to FIG. 1, the weighing scale 106 may be coupled to the mount 104 and be configured to output a signal corresponding to a weight of contents in the canister 102. In one implementation, the mount 104 of the system 100 is configured to rest on a horizontal surface, and the weighing scale 106 is coupled to the mount 104 opposite the canister 102 and outputs a signal corresponding to the weight of the mount 104, the computing device 131, the canister 102, fluid in the canister, etc. above, as shown in FIG. 2A. In this implementation, the weighing scale 104 can include a footing or resilient friction pad 196 configured to sit on a horizontal surface and a strain gauge 198 interposed between the mount 104 and the footing 196. In another implementation, the system is configured to hang, such as from a hook on the operating room table or IV pole, and the weighing scale is arranged between the lid and the hook and configured to output a signal corresponding to the weight of the mount, the computing device, the canister, the lid, fluid in the canister, etc. below. However, the system can include a weighing scale of any other type and coupled to the mount or to the canister in any other suitable way.

In some embodiments, the processor may receive weight information from the scale in a continuous or a variable manner. The sampling rate for the weight may be in the range of about 1000 Hz to about once every 5 minutes, or about 60 Hz to about 1 Hz. In some variations, when the detected rate of fluid weight increase is higher or in a certain range, the sampling rate of the scale may be increased, as well as image capture rate or illumination rate of the imaging system.

The scale may also be used to indicate other states of events relating to canister use. For example, the complete unweighting of the scale, or reduction of weight below the tare weight of the canister, may be used to indicate removal of the canister. During use of the vacuum system, the detected weight may increase in a generally linear fashion while suctioning liquid material, but may exhibit some variation when suctioning mixtures of liquid and solid or semi-solid materials or tissue. The weight may also oscillate when the suction device is used at a liquid/air interface and the processor of the system may be configured to detect such states and to wait for the oscillations to stop before reporting any weight changes.

1.6 Processor

As noted previously, the system typically comprises a processor that may be configured to transform an image captured by the color camera into an estimated concentration of a blood component in a fluid within the canister and to estimate an amount of the blood component in the canister based on the estimated concentration of the blood component and an output of the weighing scale. Generally, the processing functions to locally execute one or more aspects of the method described below.

In the implementation described above in which the optical emitter 128 and the camera 130 are integrated into a standalone computing device 131, as shown in FIG. 1, the processor 132 can be similarly integrated into the computing device 131. In this implementation, the computing device 131 can communicate with the weighing scale 106 and/or with an electromechanical valve coupled to the lid or in the lid via a wired connection to a port in the computing device. Alternatively, the system can include a short-range wireless communication module, such as NFC or Bluetooth or wireless USB, electrically coupled to the weighing scale and/or to the electromechanical valve, and the computing device 131 can wirelessly pair with the wireless communication module to receive outputs from the weighing scale and/or to control the state of the valve.

In another variation, the camera, the optical emitter, the digital display, and the processor are integrated into the mount. However, the system can include any other integrated or discrete elements that cooperate to collect fluid from a suction wand, to weigh the fluid, to image the fluid, to transform images of the fluid into estimations of the quality of the fluid, and to generate estimations of the quantity of one or more blood components in the fluid over time.

2. Method

Figure 3:
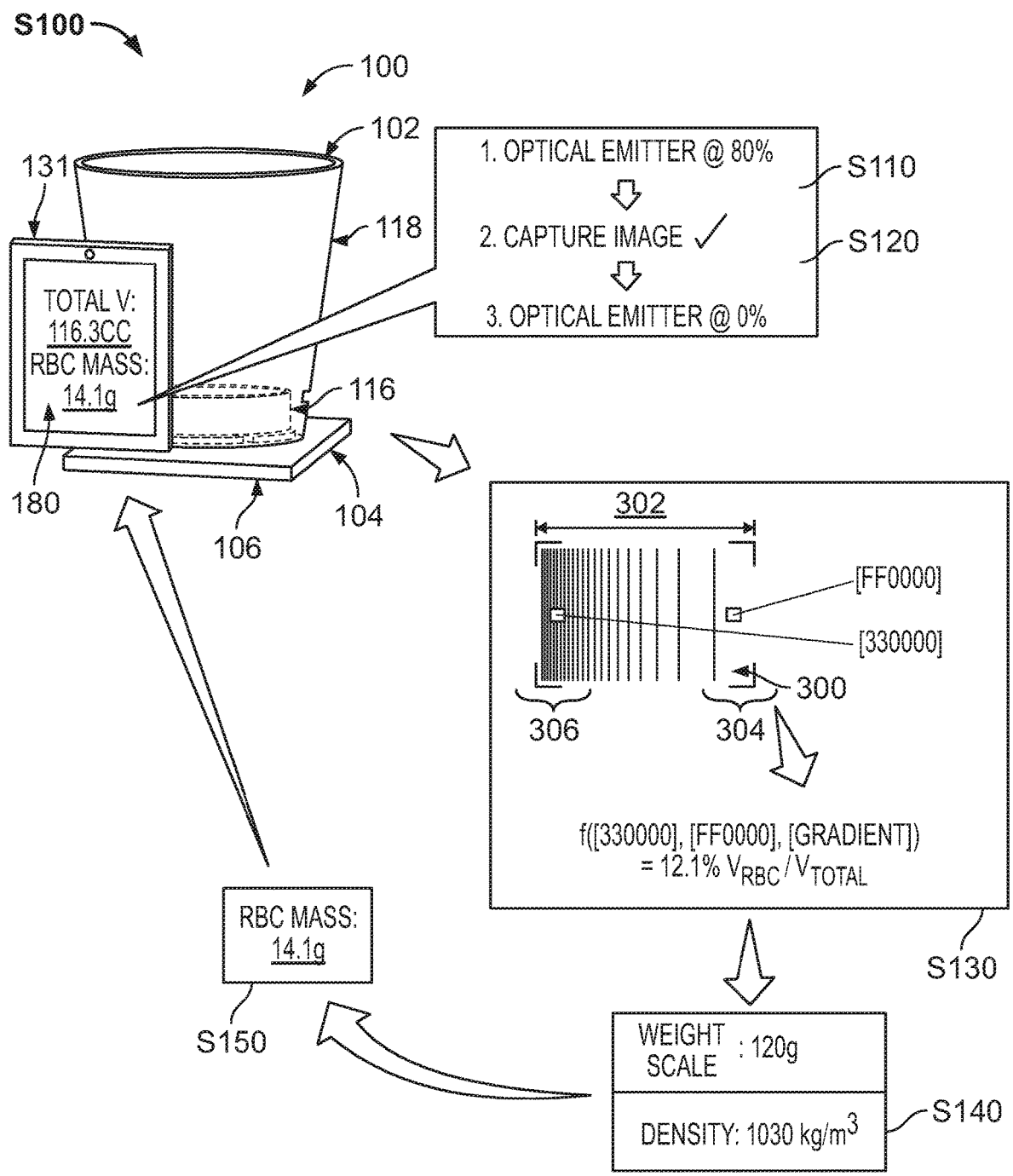
FIG. 3 is a schematic representation of a method for assessing a canister.

FIG. 3 depicts an illustrative method that may be suitable for use with the systems described herein. As shown there, a method S100 for estimating an amount of a blood component in a volume of fluid may include illuminating an insert 116 within a canister 102 according to an illumination schedule; capturing an image of the insert (via an optical detector or camera offset from the optical emitter), estimating a concentration of a blood component in a fluid within the canister e.g., based on the illumination schedule, color intensities of pixels in the image, and a color gradient from a first region to a second region in the image, where the first region corresponds to proximity to the optical emitter, and the second region corresponds to remoteness from the optical emitter.

2.1 Applications

Generally, one or more portions the method may be executed locally by the system 100 described above to automatically capture an image of a (sub)volume of fluid contained in a canister 102 and to transform absolute color values in the image and/or color gradients across pixels in the image into a quantitative estimation of a concentration of a blood component in the canister 102. For example, the system 100 may transform an image into an estimation of a mass per unit volume of hemoglobin, a volume fraction of red blood cells, or a volume fraction of whole blood, etc. of fluid contained in the canister. In particular, the system 100 may actuate an optical emitter to illuminate the volume of fluid in S110, triggers a camera to capture an image in S120, and processes the image to generate a blood component concentration estimation in S130. As noted previously, the light source or optical emitter and the camera or optical detector may be provided in the computing device 131, or may be integrated into the mount 104.

The method described herein may be executed locally by the system, e.g. the computing device 131, for estimating an amount of a blood component in a volume of fluid described above. However, portions of the method may additionally or alternatively be executed remotely from the system, such as by another local computing device connected to the system, by a local distributed network, or by a remote server.

2.2 Image Capture

The method may further comprise at S110 illuminating an insert 116 within a canister 104 according to an illumination schedule (e.g., using an optical emitter); and at S120, capturing an image of the insert 116 (e.g., using an optical detector). Generally, the system is configured to illuminate the reflective insert 116 within the canister 102—and therefore a volume of fluid between the reflective insert and the camera—and to capture an image of the illuminated volume of fluid located between the insert 116 and the wall 142 of the canister 102.

In one implementation, to capture an image of a volume of fluid in the canister, the system 100 powers on the optical emitter at a static, preset illumination power in S110, triggers the camera to capture an image in S120, and then deactivates the optical emitter. The power level may be in the range of 1 lumen to 1,000 lumens, or about 3 lumens to about 100 lumens, or about 3 lumens to about 50 lumens, or about 5 lumens to about 20 lumens, or about 15 lumens to 30 lumens, about or may be anywhere from 1% to 100% or about 30% to about 100%, or about 70% to about 100% of the light source's maximum power.

In another implementation, to capture an image of a volume of fluid in the canister 102, the system 100 first activates the optical emitter at a select illumination power, such as by pulse-width modulating the optical emitter at a selected duty cycle, in order to achieve target brightness in an image subsequently captured by the camera. For example, the system 100 can pulse-width modulate the optical emitter at frequency greater than a fastest shutter speed implemented by the camera (e.g., 500 Hz for a camera operable at a maximum shutter speed of $\frac{1}{100}$ s). The system then triggers the camera to capture an image in Block S120, such as 0.002 second after the optical emitter is activated in Block S110. Once the image is recorded in Block S120, the system can deactivate the optical emitter.

In some other embodiments, the processor may be configured to initiate image capture upon a signal from the scale indicating a change in the weight of the canister contents.

In the foregoing implementation, the system 100 can progress through a set of duty cycles—such as down from 100% duty or up from 0% in 1%, 5%, 10%, 20% duty increments—and capture an image at each duty until the camera captures an image that meets one or more target color parameters, such as a lightest color limit, a darkest color limit, or target color gradient between the first region and the second region of the image. In one exemplary implementation, the system can increase the duty cycle of the optical emitter—starting at 0%—and capture an image for each duty cycle through the camera until a captured image contains a contiguous horizontal line of pixels containing less than a threshold number of black pixels or pixels darker than a threshold dark color value. For example, once an image is captured by the camera, the system can scan a single horizontal line of pixels centered vertically in the image and count a number of consecutive pixels (or a total number of pixels) along the scan line containing the color black or containing a color value less than (i.e., darker than) a threshold darkness value. In this example, if the number of consecutive pixels (or total number of pixels) along the scan line exceeds a threshold count, the system can reject the image, increase the duty cycle of the optical emitter, capture a subsequent image through the camera, and similarly process the subsequent image. The system can repeat this process until a final image with a number of consecutive pixels (or total number of pixels) along a scan line less than the threshold count is captured. The system can then process this final image in Block S130, as described below.

In another exemplary implementation, the system can decrease the duty cycle of the optical emitter—starting from 100%—and capture an image for each duty cycle through the camera until a captured image contains a contiguous horizontal line of pixels containing less than a threshold number of white pixels or pixels lighter than a threshold light color value.

In the foregoing exemplary implementations, for a subsequent sampling period, the system can repeat the foregoing process, starting with a low duty cycle (e.g., 0%) or a high duty cycle (e.g., 100%) at the optical emitter and then increase or decrease the duty cycle, respectively, until a suitable image is captured at the camera. Alternatively, the system can begin a new imaging period by setting the optical emitter to implement a last duty cycle from the preceding imaging period. The system can then capture a first image in the new imaging period through the camera, either increase or decrease the duty cycle of the optical emitter if the first image contains an excess number of black or dark pixels or if the first image contains an excess number of white or light pixels, respectively, capture and process a subsequent image, and then repeat the foregoing until an image containing color data of suitable quality is achieved. In these implementations, the system can thus vary the illumination power output by the optical emitter and process images captured under various illumination powers in order to identify and record an image containing a suitable quality of color data that can be transformed into a quality (e.g., a blood component concentration) of a volume of fluid in the canister.

Additionally or alternatively, the system may set an illumination power (by setting a duty cycle) of the optical emitter and then vary the shutter speed of the camera—and therefore an exposure of an image captured with the camera—to achieve an image with a quality of color data suitable for transformation into a quality of the volume of fluid in the canister. For example, the system may operate the optical emitter at a duty cycle of 100%; decrease the shutter speed of the camera (e.g., from $\frac{1}{200}$ s to $\frac{1}{100}$ s, then $\frac{1}{30}$ s, $\frac{1}{20}$ s, $\frac{1}{15}$ s, $\frac{1}{12}$ s, etc.); and capture an image through the camera for each shutter speed until a captured image contains a contiguous horizontal line of pixels containing less than a threshold number of black pixels or pixels darker than a threshold dark color value.

In the foregoing implementations, the system may implement any other method or technique to set an illumination power, a shutter speed, or any other illumination or image-capture parameter for the imaging system. Similarly, the system may implement any other method or technique to confirm that an image captured by the camera—for a given set of illumination and image-capture parameters—contains sufficient color data for transformation into a quality of fluid within the canister. The system may also manipulate multiple illumination and image capture parameters—such as both a duty of the optical emitter and a shutter speed of the camera—to achieve a target color quality in an image.

The system can therefore capture multiple images during a single imaging period and discard all but a single image containing sufficient color data for transformation into a quality (e.g., a blood component concentration) of a volume of fluid contained in the canister. The system may tag this select image with illumination and/or image capture parameters executed by the imaging system to capture the select image, such as the duty implemented by the optical emitter and/or the shutter speed implemented by the camera when the select image was captured. In order to transform the select image into a fluid quality in Block S130, the system can then select a set of template images based on these illumination and image capture parameters for comparison to the select image or insert these illumination and image capture parameters into a parametric model that is then applied to color values in select images, as described below.

In one variation, the system captures multiple images at different illumination and/or image-capture parameters in Blocks S110 and S120. For example, in a single imaging period, the system may: set the optical emitter at 0% duty and capture a first image; set the optical emitter at 50% duty and capture a second image; and then set the optical emitter at 100% duty and capture a third image. In another example, the system may: step the duty of the optical emitter upward from a minimum duty (e.g., 0%); capture an image at each duty step; store a first image including a total number of black pixels less than a threshold number of black pixels; and store a last image including a total number of white pixels less than a threshold number of white pixels (or vice versa). In yet another example, the system may: set the duty cycle of the optical emitter (e.g., at a static value of 80%); step the shutter speed downward from a maximum shutter speed (e.g., $\frac{1}{200}$ s); capture an image at each shutter speed; store a first image including a total number of black pixels less than a threshold number of black pixels; and store a last image including a total number of white pixels less than a threshold number of white pixels (or vice versa).

However, the system may manipulate any other illumination and/or image capture parameter across a set of images. The system may then process this set of images in Block S130 to estimate a quality of the fluid within the canister during the corresponding imaging period.

2.3 Blood Component Concentration

Block S130 of the method depicts, color intensities of pixels in the image 300, and a color gradient 302 from a first region 304 to a second region 306 in the image 300, estimating a concentration of a blood component in a fluid within the canister, the first region 304 corresponding to proximity to the optical emitter, and the second region 306 corresponding to remoteness from the optical emitter. Generally, in Block S130, the system transforms color values contained in pixels in an image 300 captured by the camera into one or more of: a concentration of red bloods cells; a concentration of hemoglobin; a proportion of whole blood cells to lysed red blood cells (or free hemoglobin); a concentration of whole blood; a concentration of plasma; a concentration of white blood cells; etc. in a volume of fluid contained in the canister. In particular, the system can implement parametric and/or non-parametric (e.g., template-matching) techniques to transform color data contained in an image 300 captured by the camera into a blood component concentration value for a volume of fluid contained in the canister, such as described, for example, in U.S. patent application Ser. No. 13/544,664 and Ser. No. 13/738,919.

In one implementation, the system implements template matching techniques to match one or more color values (e.g., intensity in the red color space) in an image captured by the camera to a template image of a fluid of known blood component concentration and stored in (local or remote) memory. In one example implementation, the system can match a color gradient from a first side of the image (corresponding to a shortest distance to the optical emitter) to an opposite side of the image (corresponding to a greatest distance from the optical emitter) to a template gradient of one or more known blood component proportions. In this exemplary implementation, the system may select a single template image containing a lightest color, a darkest color, and/or a linear or non-linear color gradient nearest the lightest color, darkest color, and/or color gradient represented in the current image and assign one or more blood component concentration values associated with the template image to the current image. Similarly, the system may select two or more template images exhibiting lightest colors, darkest colors, and/or color gradients nearest those of the current image and then average blood component concentration values associated with these template images to generate an estimation of a blood component concentration in the canister at a time the current image was captured.

In the foregoing implementation, the system may apply template images from multiple template image sets—each image template set corresponding to a subset of known blood component concentration values—to the current image in order to generate estimations of multiple blood component concentrations representative of a volume of fluid contained in the canister from a single image of the canister. For example, the system may match a difference between a lightest color value and a darkest color value in the current image to a template image in a first template image set to generate an estimation of the concentration of hemoglobin in the volume of fluid in the canister; the system may then match a non-linear color gradient between the first side of the image and the second side of the image to a template image in a second template image set to generate an estimation of the proportion of lysed red blood cells in the volume of fluid in the canister.

Furthermore, in this implementation, the system may select or filter available template images based on illumination and image-capture parameters implemented by the imaging system to capture the current image. For example, the system may set the duty of the optical emitter at 70% percent, capture an image, and then select a template image set containing template images captured by similar systems with optical emitters operating at 70% duty. In another example, the system may set the duty of the optical emitter at 100% percent, set the shutter speed of the camera at ½₀ s, capture an image, and then select a template image set containing template images captured by similar systems with optical emitters operating at 100% duty and cameras operating at a shutter speed of ½₀ s.

However, in this implementation, the system may implement any other method or technique to select a template image of known blood component concentration and to match the template image to a current image captured by the camera to generate an estimation of a blood component concentration in a volume of fluid contained in the canister at a time the current image was captured.

In another implementation, the system passes quantitative data represented in one or more pixels in the current image into a parametric model that outputs a quantitative estimation of the concentration of one or more blood components in a volume of fluid contained in the canister, as shown in FIG. 3. For example, the system may pass a color value in a single lightest pixel (or in a small cluster of lightly-colored pixels) and a color value in a single darkest pixel (or in a small cluster of relatively dark pixels) in the current image into the parametric model. In another example in which the camera captures an image 2000 pixels wide and 1000 pixels tall, the system can: separate the current image into ten 200-pixel-wide, 1000-pixel tall columns; average the intensity of each column in the red, green, and blue component spaces; and pass these thirty intensity values into a parametric model that transforms these values into an estimation of the concentration of one or more blood components in the volume of fluid in the canister at the time the current image was captured.

The system may also calculate coefficients of a linear, logarithmic, polynomial, power, or other trendline of the color gradient from the first region of the image (e.g., a pixel or pixel cluster of lightest color) to the second region of the image (e.g., a pixel or pixel cluster of darkest color) and pass these coefficient values into a parametric model. The system may also identify a trendline type (e.g., linear, logarithmic, or polynomial, etc.) that best fits the color gradient represented in the current image, select a parametric model for the identified trendline type, and then pass coefficients of a trendline of the identified trendline type into the selected parametric model to generate an estimation of the concentration of the blood component in the canister.

In this implementation, in addition to color values of pixels in the current image, the system may also pass illumination and/or image-capture parameters implemented by the imaging system to capture the current image—such as a duty of the optical emitter or the shutter speed of the camera—into the parametric model. Alternatively, the system may select a particular parametric model from a set of available parametric models based on the illumination and/or image-capture parameters implemented by the imaging system to capture the current image; the system may then pass color values of pixels in the current image into the selected parametric model to output an estimation of a blood component concentration in the canister.

In the variation above in which the system captures multiple images through the camera in a single imaging period, the system may also implement any of the foregoing methods and techniques to compare absolute color values or color gradients across two or more images in a set of images. For example, the system may capture two images of the volume of fluid in the canister under two distinct lighting conditions (e.g., 20% duty and 80% duty at the optical emitter) and then characterize a difference in the color gradients across both images as a concentration of whole red blood cells and a concentration of free hemoglobin in the volume of fluid in the canister.

However, the system may implement any other parametric or non-parametric techniques to transform color data contained in one or more images captured by the camera into an estimation of a quality of a volume of fluid contained in the canister.

2.4 Image Quality

In one variation, the system determines a quality of an image output, as depicted in Block S120, and selectively discards this image or passes this image on to the next step of the process. In one implementation, the system scans the image vertically (e.g., along one or more vertical columns of pixels in the image) for a sharp shift in color value from a lower region of the image to an upper region of the image. The system may then correlate this color shift with collection of sediment on the bottom of the vessel, discard the image, and/or trigger manual or automatic removal of sediment from the field of view of the camera if such a color shift is detected in the image. In particular, due to proximity of the optical emitter to the camera, as sediment collects on the bottom of the canister and obscures the field of view of the camera, sediment may similarly obscure projection of light from the optical emitter onto the reflective insert such that sediment in the field of view of the camera remains substantially dim compared to the reflective insert when the optical emitter is actuated. Therefore, an image captured by the camera after sediment has collected in the field of view of the camera may contain a contiguous column of relatively dark pixels corresponding to a segment, extending upwardly from the bottom of the image, and rapidly transitioning into a contiguous column of relatively bright pixels corresponding to the reflective insert (and to fluid between the wall of the canister and the reflective insert). The system may scan one or more vertical columns of pixels in an image captured by the camera and then discard the image as containing insufficient color data of the fluid if a column of pixels in the image includes a transition from a line of dark pixels to a line of light pixels (or if the image includes more than a threshold number of dark pixels in a vertical column of dark pixels below a line of light pixels).

In one example, if a color shift is detected in an image, the system can issue an audible or visual prompt (e.g., through the display) to agitate the contents of the vessel. The system can then sample an integrated accelerometer to determine if the canister has been agitated or continue to capture and analyze images to determine if sediment has been removed from the field of view of the camera. Alternatively, if a color shift indicative of obscuration of the camera is detected in an image recently captured by the camera, the system can automatically activate an agitator—as described above—to mix contents and redistribute sediment within the canister prior to capturing. For example, the system can activate the agitator for a preset period of time (e.g., 10 seconds) or until images captured by the camera no longer exhibit such a sharp shift in color value. In this example, once a sharp color value shift is no longer detected in the field of view of the color system, the system can deactivate the agitator, pause for a period of time (e.g., five seconds) to allow fluid within the canister to slow, and then execute Blocks S110, S120, and S130 as described above to capture and process an image of fluid in canister.

Furthermore, in this variation, if sediment is detected in a current image but the current image contained sufficient color data to provide a reliable estimation of the concentration of a blood component in the canister, the system can remove (e.g., crop) a region of the current image correlated with obscuration by sediment and pass the remainder of the current image to Block S130 for processing. However, the system may implement any other method or technique to confirm the quality of images captured by the camera and selectively pass on and/or reject these images.

2.5 Blood Component Quantity

While capturing images in Block S120, the system may also sample the weighing scale and apply a value output by the weighing scale to the blood component concentration value to estimate a quantity (e.g., a volume, a mass) of the blood component in the canister in Block S140. In one implementation, the system 100 continuously samples the weighing scale and records outputs of the weighing scale 106 with corresponding timestamps in memory. In this implementation, for an image captured in Block S120 and processed in Block S130, the system 100 can retrieve—from memory—a weighing scale output value (e.g., weight) recorded at a time nearest a time that the image 300 was captured. (The system 100 can also retrieve multiple weighing scale outputs recorded around the time that the image was captured and then average these values.) The system 100 can then divide this weighing scale output value for the imaging period by a static estimated density of fluid collected in the canister 102 (e.g., 1030 kg/m$^3$ for a mixture of saline and blood) to estimate the volume of fluid in the canister. By then multiplying this estimated volume by the blood component concentration, the system can estimate the volume (or mass) of the blood component (e.g., hemoglobin, red blood cells) in the canister, as depicted in Block S150.

The system can repeat Blocks S110, S120, S130, S140, and S150 throughout an operation—such as at a rate of 1 Hz—in order to update estimations of a volume of fluid in the canister, a quality of the volume of fluid, and/or a quantity of a blood component in the canister over time.

2.6 Visual Feedback

Throughout operation, as shown in Block S100, the system 100 may update an integrated display 180 over time to visually indicate a current estimated volume of fluid in the canister 102, a current estimated quality of the volume of fluid, and/or a current estimated quantity of the blood component in the canister 102, as shown in FIG. 3. The system 100 may also render prompts on the display 180, such as a prompt to empty the canister 102 or a prompt to agitate the canister 102 due to collection of sediment in front of the imaging system.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. When implemented as a system, such system may comprise, inter alia, components such as software modules, general-purpose CPU, RAM, etc. found in general-purpose computers, and/or FPGAs and/or ASICs found in more specialized computing devices. In implementations where the innovations reside on a server, such a server may comprise components such as CPU, RAM, etc. found in general-purpose computers. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

In the present description, the terms component, module, device, etc. may refer to any type of logical or functional circuits, blocks and/or processes that may be implemented in a variety of ways. For example, the functions of various circuits and/or blocks can be combined with one another into any other number of devices. Or, the devices can comprise programming instructions transmitted to a general purpose computer or to processing/graphics hardware via a transmission carrier wave. Also, the devices can be implemented as hardware logic circuitry implementing the functions encompassed by the innovations herein. Finally, the devices can be implemented using special purpose instructions (SIMD instructions), field programmable logic arrays or any mix thereof which provides the desired level performance and cost.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

As a person skilled in the art will recognize from the previous detailed description and from the figures and claims, modifications and changes can be made to the embodiments of the invention without departing from the scope of this invention as defined in the following claims.

The invention claimed is:
1. Apparatus comprising:
 a canister receptacle to receive a canister, the canister to receive fluid from a patient;
 a weight measurement element arranged to measure weight of the canister including the fluid;

an image capture device to capture of an image of the fluid, the capture device being triggered based on weight information from the weight measurement element; and a communication interface to communicate the weight information and image data to a processing unit that triggers the image capture device, the processing unit being configured to determine a hemoglobin value of the fluid in the canister based on the weight and the image of the fluid.

2. The apparatus of claim 1, wherein the processing unit is configured to trigger the image capture device based on a change in the weight of the canister.

3. The apparatus of claim 1, wherein the processing unit is configured to receive the captured image in response to the image capture device being triggered based on a change in the weight of the canister.

4. The apparatus of claim 1, wherein the processing unit is configured to determine a hemoglobin value of the fluid in the canister based on the image of the fluid, and to modify the hemoglobin value of the fluid.

5. The apparatus of claim 1, wherein the processing unit is configured to initiate a draining of the fluid from the canister, and to set a reference weight of the canister in response to completion of the initiated draining of the fluid.

6. The apparatus of claim 1, wherein the processing unit is configured to detect removal of the canister from the canister receptacle based on the weight information, and to store at least one of a fluid concentration value of the fluid in the canister or a fluid volume value of the fluid in the canister in response to the detected removal of the canister.

7. The apparatus of claim 1, wherein the processing unit is configured to detect removal of the canister from the canister receptacle based on the weight information, and to reset at least one of a counter corresponding to the fluid or a register corresponding to the fluid in response to the detected removal of the canister.

8. The apparatus of claim 1, wherein the processing unit is integral with the apparatus.

9. The apparatus of claim 1, wherein the processing unit is remote from the image capture device and the weight measurement element.

10. The apparatus of claim 1, wherein the image is of a sub-volume of the fluid in the canister.

11. The apparatus of claim 1, wherein the processing unit is configured to transform at least one of absolute color values in the image or color gradients across pixels in the image into a quantitative estimation of a concentration of a blood component in the fluid.

12. The apparatus of claim 1, wherein the processing unit is configured to trigger an optical emitter to assist the image capture device to capture the image.

13. The apparatus of claim 12, wherein the optical emitter is configured to illuminate a reflective insert in the canister, and the image capture device is configured to capture the image of the fluid between the reflective insert and a wall of the canister.

14. The apparatus of claim 1, wherein the processing unit is configured to estimate a concentration of a blood component in the fluid based on the weight.

15. The apparatus of claim 1, wherein a display is caused to be updated to visually indicate at least one of a current estimated volume of the fluid in the canister, a current estimated quality of the volume of the fluid, or a current estimated quantity of a blood component in the canister.

16. A system comprising:
a canister;
a scale;
an imaging device; and
a processor configured to cause the imaging device to capture an image of fluid in the canister based on weight information from the scale, the processor being further configured to determine a hemoglobin value of the fluid in the canister based on the weight and the image of the fluid.

17. The system of claim 16, further comprising:
a communication module configured to provide the weight information from the scale to the processor.

18. The system of claim 16, wherein the processor is configured to cause the imaging device to capture the image of the fluid in the canister in response to the weight information from the scale indicating a change in a weight of the canister.

19. The system of claim 16, wherein the processor is configured to initiate a draining of the fluid from the canister, and to set a reference weight of the canister in response to completion of the initiated draining of the fluid.

20. The system of claim 16, wherein the imaging device is arranged to capture the image of the fluid through a first aperture in a wall between the canister and the imaging device.

21. The system of claim 20, further comprising:
an optical emitter configured to illuminate the fluid through a second aperture in the wall, the second aperture being optically isolated from the first aperture in the wall.

22. A method comprising:
monitoring, by one or more processors, a weight of a canister that contains fluid based on weight information from a scale;
detecting, by the one or more processors, a change in the weight of the canister that contains the fluid;
causing, by the one or more processors, an imaging device to capture an image of the fluid in the canister in response to the change in the weight of the canister;
providing, by the one or more processors, an estimated volume of the fluid in the canister based on the image caused to be captured in response to the change in the weight of the canister; and
determining, by the one or more processors, a hemoglobin value of the fluid in the canister based on the weight and the image of the fluid.

23. The method of claim 22, further comprising:
estimating an amount of a fluid component within the estimated volume of the fluid in the canister; and
providing the estimated amount of the fluid component.

24. Apparatus comprising:
a canister receptacle to receive a canister, the canister to receive fluid from a patient;
a weight measurement element arranged to measure weight of the canister including the fluid;
an image capture device to capture of an image of the fluid, the capture device being triggered based on weight information from the weight measurement element; and
a communication interface to communicate the weight information and image data to a processing unit that triggers the image capture device, the processing unit being configured to determine a hemoglobin value of the fluid in the canister based on the image of the fluid, and to modify the hemoglobin value of the fluid.

25. A system comprising:
a canister;
a scale;

an imaging device; and a processor configured to cause the imaging device to capture an image of fluid in the canister based on weight information from the scale, the processor being further configured to determine a hemoglobin value of the fluid in the canister based on the image of the fluid, and to modify the hemoglobin value of the fluid.

26. A method comprising:

monitoring, by one or more processors, a weight of a canister that contains fluid based on weight information from a scale;

detecting, by the one or more processors, a change in the weight of the canister that contains the fluid;

causing, by the one or more processors, an imaging device to capture an image of the fluid in the canister in response to the change in the weight of the canister;

providing, by the one or more processors, an estimated volume of the fluid in the canister based on the image caused to be captured in response to the change in the weight of the canister;

determining, by the one or more processors, a hemoglobin value of the fluid in the canister based on the image of the fluid; and modifying, by the one or more processors, the hemoglobin value of the fluid.

27. Apparatus comprising:

a canister receptacle to receive a canister, the canister to receive fluid from a patient;

a weight measurement element arranged to measure weight of the canister including the fluid;

an image capture device to capture of an image of the fluid, the capture device being triggered based on weight information from the weight measurement element; and a communication interface to communicate the weight information and image data to a processing unit that triggers the image capture device, the processing unit being configured to initiate a draining of the fluid from the canister, and to set a reference weight of the canister in response to completion of the initiated draining of the fluid.

28. A system comprising:

a canister;

a scale;

an imaging device; and a processor configured to cause the imaging device to capture an image of fluid in the canister based on weight information from the scale, the processor being further configured to initiate a draining of the fluid from the canister, and to set a reference weight of the canister in response to completion of the initiated draining of the fluid.

29. A method comprising:

monitoring, by one or more processors, a weight of a canister that contains fluid based on weight information from a scale;

detecting, by the one or more processors, a change in the weight of the canister that contains the fluid;

causing, by the one or more processors, an imaging device to capture an image of the fluid in the canister in response to the change in the weight of the canister;

providing, by the one or more processors, an estimated volume of the fluid in the canister based on the image caused to be captured in response to the change in the weight of the canister;

initiating, by the one or more processors, a draining of the fluid from the canister; and setting, by the one or more processors, a reference weight of the canister in response to completion of the initiated draining of the fluid.

30. Apparatus comprising:

a canister receptacle to receive a canister, the canister to receive fluid from a patient;

a weight measurement element arranged to measure weight of the canister including the fluid;

an image capture device to capture of an image of the fluid, the capture device being triggered based on weight information from the weight measurement element; and a communication interface to communicate the weight information and image data to a processing unit that triggers the image capture device, the processing unit being configured to detect removal of the canister from a canister receptacle based on the weight information, and to store at least one of a fluid concentration value of the fluid in the canister or a fluid volume value of the fluid in the canister in response to the detected removal of the canister.

31. A system comprising:

a canister;

a scale;

an imaging device; and a processor configured to cause the imaging device to capture an image of fluid in the canister based on weight information from the scale, the processor being further configured to detect removal of the canister from a canister receptacle based on the weight information, and to store at least one of a fluid concentration value of the fluid in the canister or a fluid volume value of the fluid in the canister in response to the detected removal of the canister.

32. A method comprising:

monitoring, by one or more processors, a weight of a canister that contains fluid based on weight information from a scale;

detecting, by the one or more processors, a change in the weight of the canister that contains the fluid;

causing, by the one or more processors, an imaging device to capture an image of the fluid in the canister in response to the change in the weight of the canister;

providing, by the one or more processors, an estimated volume of the fluid in the canister based on the image caused to be captured in response to the change in the weight of the canister;

detecting, by the one or more processors, removal of the canister from a canister receptacle based on the weight information; and storing, by the one or more processors, at least one of a fluid concentration value of the fluid in the canister or a fluid volume value of the fluid in the canister in response to the detected removal of the canister.

33. Apparatus comprising:

a canister receptacle to receive a canister, the canister to receive fluid from a patient;

a weight measurement element arranged to measure weight of the canister including the fluid;

an image capture device to capture of an image of the fluid, the capture device being triggered based on weight information from the weight measurement element; and a communication interface to communicate the weight information and image data to a processing unit that triggers the image capture device, the processing unit being configured to detect removal of the canister from the canister receptacle based on the weight information, and to reset at least one of a counter corresponding to the fluid or a register corresponding to the fluid in response to the detected removal of the canister.

34. A system comprising:
a canister;
a scale;
an imaging device; and
a processor configured to cause the imaging device to capture an image of fluid in the canister based on weight information from the scale, the processor being further configured to detect removal of the canister from a canister receptacle based on the weight information, and to reset at least one of a counter corresponding to the fluid or a register corresponding to the fluid in response to the detected removal of the canister.

35. A method comprising:
monitoring, by one or more processors, a weight of a canister that contains fluid based on weight information from a scale;
detecting, by the one or more processors, a change in the weight of the canister that contains the fluid;
causing, by the one or more processors, an imaging device to capture an image of the fluid in the canister in response to the change in the weight of the canister;
providing, by the one or more processors, an estimated volume of the fluid in the canister based on the image caused to be captured in response to the change in the weight of the canister;
detecting, by the one or more processors, removal of the canister from a canister receptacle based on the weight information; and
resetting, by the one or more processors, at least one of a counter corresponding to the fluid or a register corresponding to the fluid in response to the detected removal of the canister.

36. Apparatus comprising:
a canister receptacle to receive a canister, the canister to receive fluid from a patient;
a weight measurement element arranged to measure weight of the canister including the fluid;
an image capture device to capture of an image of the fluid, the capture device being triggered based on weight information from the weight measurement element; and
a communication interface to communicate the weight information and image data to a processing unit that triggers the image capture device, the processing unit being configured to transform at least one of absolute color values in the image or color gradients across pixels in the image into a quantitative estimation of a concentration of a blood component in the fluid.

37. A system comprising:
a canister;
a scale;
an imaging device; and
a processor configured to cause the imaging device to capture an image of fluid in the canister based on weight information from the scale, the processor being further configured to transform at least one of absolute color values in the image or color gradients across pixels in the image into a quantitative estimation of a concentration of a blood component in the fluid.

38. A method comprising:
monitoring, by one or more processors, a weight of a canister that contains fluid based on weight information from a scale;
detecting, by the one or more processors, a change in the weight of the canister that contains the fluid;
causing, by the one or more processors, an imaging device to capture an image of the fluid in the canister in response to the change in the weight of the canister;
providing, by the one or more processors, an estimated volume of the fluid in the canister based on the image caused to be captured in response to the change in the weight of the canister; and
transforming, by the one or more processors, at least one of absolute color values in the image or color gradients across pixels in the image into a quantitative estimation of a concentration of a blood component in the fluid.

39. Apparatus comprising:
a canister receptacle to receive a canister, the canister to receive fluid from a patient;
a weight measurement element arranged to measure weight of the canister including the fluid;
an image capture device to capture of an image of the fluid, the capture device being triggered based on weight information from the weight measurement element; and
a communication interface to communicate the weight information and image data to a processing unit that triggers the image capture device, the processing unit being configured to estimate a concentration of a blood component in the fluid based on the weight.

40. A system comprising:
a canister;
a scale;
an imaging device; and
a processor configured to cause the imaging device to capture an image of fluid in the canister based on weight information from the scale, the processor being further configured to estimate a concentration of a blood component in the fluid based on the weight.

41. A method comprising:
monitoring, by one or more processors, a weight of a canister that contains fluid based on weight information from a scale;
detecting, by the one or more processors, a change in the weight of the canister that contains the fluid;
causing, by the one or more processors, an imaging device to capture an image of the fluid in the canister in response to the change in the weight of the canister;
providing, by the one or more processors, an estimated volume of the fluid in the canister based on the image caused to be captured in response to the change in the weight of the canister; and
estimating, by the one or more processors, a concentration of a blood component in the fluid based on the weight.

* * * * *